United States Patent [19]
Rich et al.

[11] Patent Number: 5,639,852
[45] Date of Patent: Jun. 17, 1997

[54] IMMUNOSTIMULATORY AGENTS

[75] Inventors: Daniel H. Rich; Miroslav Malkovsky; Yvonne M. Angell, all of Madison, Wis.

[73] Assignee: Wisconsin Alumni Research Foundation, Madison, Wis.

[21] Appl. No.: 299,504

[22] Filed: Sep. 1, 1994

[51] Int. Cl.$^6$ .......................... A61K 38/12; A61K 45/05
[52] U.S. Cl. ...................... 530/317; 424/278.1; 530/321
[58] Field of Search ........................... 530/317, 321; 514/11, 885; 424/278.1

[56] References Cited

U.S. PATENT DOCUMENTS

| | | | |
|---|---|---|---|
| 4,384,996 | 5/1983 | Bollinger et al. | 260/112.5 |
| 4,771,122 | 9/1988 | Seebach | 530/317 |
| 4,814,323 | 3/1989 | Andrieu et al. | 514/11 |
| 4,914,188 | 4/1990 | Dumont et al. | 530/317 |
| 5,284,826 | 2/1994 | Eberle et al. | 514/11 |

FOREIGN PATENT DOCUMENTS

484281A2 10/1991 European Pat. Off. .......... C07K 7/64

OTHER PUBLICATIONS

N.A. Campbell in *Biology (3rd. ed.)*, Benjamin Cummings Publishing Company, Inc., Redwood City, CA, pp. 850–872 (1993).

L.L. Lanier, "Distribution and Function of Lymphocyte Surface Antigens," Ann. N.Y. Acad. Sci., 677:86–93 (1993).

S.B. Mizel et al., "Characterization of Lymphocyte–Activating Factor (LAF) Produced by a Macrophage Cell Line, P388D$_1$. II. Biochemical Characterization of LAF Induced by Activated T Cells and LPS," J. Immunol., 120:1504–1508 (1978).

J. Shaw et al., "Effects of Costimulator on Immune Responses in vitro," J. Immunol., 120:1974–1980 (1978).

H.S. Teh et al., "Direct Evidence for a Two–Signal Mechanism of Cytotoxic T–Lymphocyte Activation," Nature 285:163–165 (1980).

J. Shaw et al., "Cellular Origins of Co–Stimulator (IL2) and Its Activity in Cytotoxic T Lymphocyte Responses," J. Immunol., 124:2231–2239 (1980).

S. Chouaib, "Tumor Necrosis Factor α: a Costimulator for Cytotoxic Cell Differentiation," Nouv. Rev. Fr. Hematol., 33:471–475 (1991).

M.K. Jenkins et al., "CD28 Delivers a Costimulatory Signal Involved in Antigen–Specific IL-2 Production by Human T Cells," J. Immunol., 147:2461–2644 (1991).

J.D. Fraser et al., "Regulation of T–Cell Lymphokine Gene Transcription by the Accessory Molecule CD28," Mol. Cell Biol., 12:4357–4363 (1991).

L. Koulova et al., "The CD28 Ligand B7/BB1 Provides Costimulatory Signal for Alloactivation of CD4$^+$ T Cells," J. Exp. Med., 173:759–762 (1991).

(List continued on next page.)

*Primary Examiner*—Ponnathapura Achutamurthy
*Attorney, Agent, or Firm*—Medlen & Carroll

[57] ABSTRACT

Compositions and methods are described for the synthesis of novel analogs of cyclosporin A, and the use of those analogs as immunostimulatory agents.

1 Claim, 15 Drawing Sheets

[MeLeu(3-OH)$^1$,MeAla$^{4,6}$]-CsA: R$_1$=R$_2$=CH$_3$

OTHER PUBLICATIONS

J.A. Gross et al, "Identification and Distribution of the Costimulatory Receptor CD28 in the Mouse," J. Immunol., 149:380–388 (1992).

C.P. Larsen et al., "Functional Expression of the Costimulatory Molecule, B7/BB1, on Murine Dendritic Cell Populations," J. Exp. Med., 176:1215–1220 (1992).

John E. Kay, "Inhibitory Effects of Cyclosporin A on Lymphocyte Activation" in *Cyclosporin, Mode of Action and Clinical Application*, Kluwer Academic Publishers, Dordrecht, The Netherlands, pp. 1–19 (A.W. Thomson, ed.) (1989).

J.F. Borel, "Cyclosporine: Historical Perspectives" in *Cyclosporine, Biological Activity and Clinical Applications*, Grune and Stratton, Inc., Orlando, Fl. pp. 3–12, Wenger/Lafferty 26–31 (B.D. Kahan, ed.) (1984).

J.F. Borel, "The History of Cyclosporin A and Its Significance" in *Cyclosporin A*, Elsevier Biomedical Press, Amsterdam, The Netherlands, pp. 5–15, (D.J.G. White, ed.) (1982).

D.H. Rich et al., "Synthesis and Antimitogenic Activities of Four Analogues of Cyclosporin A Modified in the 1–Position," J. Med. Chem., 29:978–984 (1986).

W.J. Colucci et al., "Synthesis of D–Lysine$^8$–Cyclosporine A. Further Characterization of BOP–Cl in the 2–7 Hexapeptide Fragment Synthesis," J. Org. Chem., 55:2895–2903 (1990).

R.D. Tung et al., "BOP–Cl Mediated Synthesis of the Cyclosporine A 8–11 Tetrapeptide Fragment," J. Org. Chem., 51:3350–3354 (1986).

R.M. Wenger, "Total Synthesis of 'Cyclosporin A' and 'Cyclosporin H', Two Fungal Metabolites Isolated from the Species *Tolypocladium Inflatum* GAMS," Helv. Chim. Acta 67:502–524 (1984).

J. Coste et al., "Oxybenzotriazole Free Peptide Coupling Reagents for N–Methylated Amino Acids," Tetrahedron Lett., 32:1967–1970 (1991).

E. Gross in *The Peptides: Analysis, Synthesis, Biology (vol. 1)*, Academic Press, Inc., New York, NY, p. 332 (1979) one page.

U. Schollkopf, "Recent Applications of α–Metalated Isocyanides in Organic Synthesis," Angew. Chem., 16:339–422 (1977).

D.A. Evans et al., "Asymmetric Glycine Enolate Aldol Reactions: Synthesis of Cyclosporine's Unusual Amino Acid, MeBmt," J. Am. Chem. Soc., 108:6757–6761 (1986).

M.A. Gallop et al., "Applications of Combinatorial Technologies to Drug Discovery. 1. Background and Peptide Combinatorial Libraries," J. Med. Chem., 37:1233–1248 (1994).

E.M. Gordon et al., "Applications of Combinatorial Technologies to Drug Discovery. 2. Combinatorial Organic Synthesis, Library Screening Strategies, and Future Directions," J. Med. Chem., 37:1385–1399 (1994).

A. Karpas et al., "Inhibition of human immunodeficiency virus and growth of infected T cells by the immunosuppressive drugs cyclosporin A and FK 506," Proc. Natl. Acad. Sci., 89:8351–8355 (1992).

C. Damasco et al., "Cyclosporin A inhibits vaccinia virus replication in vitro," Arch. Virol., 134:303–319 (1994).

L. Carpino, "1–Hydroxy–7–azabenzotriazole. An Efficient Peptide Coupling Additive," J. Am. Chem. Soc., 115:4397–4398 (1992).

T. Novak et al., "Interleukin–1 Synergy with Phosphoinositide Pathway Agonists for Induction of Interleukin–2 Gene Expression: Molecular Basis of Costimulation," Mol. Cell. Biol., 10:6325–6334 (1990).

[MeLeu(3-OH)¹]-CsA: $R_1 = R_2 = CH_2CH(CH_3)_2$

[MeLeu(3-OH)¹, MeAla⁴,⁶]-CsA: $R_1 = R_2 = CH_3$

IMMUNOSTIMULATORY AGENTS

FIELD OF THE INVENTION

The present invention relates to cyclosporin derivatives to be used as agents for increasing human white blood cell activity and proliferation.

BACKGROUND OF THE INVENTION

Recent advances in molecular immunology have allowed researchers to obtain a detailed view of the cellular and molecular events which take place during the human immune response to pathogenic infection. In addition to determining the roles of the various lymphocytes in the immune response, researchers have also made some progress in mapping out their biochemical interactions, including those that involve macromolecules which may act as chemical signals to coordinate lymphocyte actions and functions.

The modern view of immunology has the T-cell as a key player in the body's specific defense mechanism. Two particular classes of T-cells, the helper T-cell ($T_H$) and the cytotoxic T-cell ($T_C$), play important roles in the both the humoral and the cell-mediated immune response. In contrast, B-lymphocytes are exclusively involved in the humoral immune response.

The humoral response is usually directed against free circulating pathogens or their antigens. Antigen-Presenting cells (APCs), such as macrophages, express fragments of digested antigens on their outer membranes often in combination with Class II MHC (Major Histo-Compatibility) proteins. Recognition of these Class II MHCs and foreign antigens trigger $T_H$ cells to proliferate. This, in turn, triggers B-cells to secrete antibodies which eventually neutralize the pathogens.

The cell-mediated response involves participation by both $T_H$ and $T_C$ cells. In this case, a cell of the body infected by the pathogen displays pathogen antigens in combination with Class I MHC proteins and thereby stimulates $T_H$ cells to activate $T_C$ cells which lyse the infected cell. [See *Biology* (3rd. ed.) Campbell, Benjamin Cummings Publishing Company, Inc. (1993)].

Because of the critical role played by the T-cells in the body's defense systems, the destruction of certain T-cell populations by the AIDS virus, effectively robs the body of its ability to defend itself. AIDS therapies have therefore focused on ways to prevent T-cell destruction and/or regenerate T-cell function. Such efforts have thus far been hampered by a lack of complete understanding of T-cell biochemistry including the elaboration of soluble mediators, i.e., cytokines.

There have been numerous studies of both biochemical mediators and cellular interactions which cause the stimulation and thereby proliferation of the body's T-cells. Much of the work has centered on discovering the identity of both the chemical signals and the membrane receptors which are directly responsible. [See Lanier "Distribution and Function of Lymphocyte Surface Antigens" Ann. N.Y. Acad. Sci. 677:86 (1993)].

It is generally agreed that T-cell activation requires more than just binding of the T-cell receptors (TCRs) to specific antigen/MHC protein combinations. [See *Biology* (3rd. ed.) Campbell, Benjamin Cummings Publishing Company, Inc. (1993)]. In particular, there has been much research on the existence of additional molecular binding events, in effect a "costimulatory" signal. These costimulatory signals, although not antigen-specific, have been shown to be critical for many stages of T-cell development, activation, and proliferation. [See Mizel "Characterization of Lymphocyte Activating Factor (LAF) Produced by Macrophage Cell Line" J. Immunol 120:1504 (1978)].

Recent immunological research has focused on two types of costimulatory signals. The first class of costimulatory signals are macromolecules which freely diffuse through the intercellular medium, where they bind to receptors on the exterior membrane of the T-cell, causing the desired metabolic changes. These free costimulators are themselves typically secreted by other lymphocytes. Shaw et al. were among the first to describe a factor, designating it by the term "Costimulator". The molecule behaved like a nonspecific second signal to induce the proliferation of T-cells, following the first signal which is an antigen. [See "Effects of Costimulator on Immune Responses IN VITRO," J. Immun. 120:1974 (1978)]. Teh et al. describe the use of the same "Costimulator" in a model system to activate cytotoxic T-cells, which were initially stimulated by antigen. [See "Direct Evidence for a Two-Signal Mechanism of Cytotoxic T-Lymphocyte Activation," Nature 285:163 (1980)]. This was also corroborated by Shaw et al. [See "Cellular Origins of Co-stimulator (IL2) and Its Activity in Cytotoxic T Lymphocyte Responses," J. Immun. 124:2231 (1980)].

"Costimulators" and other related compounds are generally peptides referred to under the general category of "Interleukins". It is currently uncertain whether compounds outside the Interleukin family can elicit T-cell metabolic changes as well. A recent article by Chouaib describes the use of purified Tumor Necrosis Factor (TNF) in the costimulation of cytotoxic cell differentiation. [See "Tumor Necrosis Factor a: a Costimulator for Cytotoxic Cell Differentiation," Nouv. Rev. Fr. Hematol. 33:471 (1991)]. However, this compound only works in combination with interleukin-2, which has the ability to stimulate T-cells without the participation of another nonspecific molecule.

A second class of costimulatory signals under investigation are membrane bound ligands typically found on other APCs, which bind to receptor proteins on the T-cell surface. In particular, there has been considerable research focused on the CD28 receptor present on the outer membrane of T-cells. [See Jenkins et al. "CD28 Delivers a Costimulatory Signal Involved in Antigen-Specific IL-2 Production By Human T Cells," J. Immun. 147:2461 (1991) and Fraser et al. "Regulation of T-cell Lymphokine Gene Transcription by the Accessory Molecule CD28," Mol. & Cell. Bio. 10:4357 (1992)]. This receptor and its activation ligand present on B-lymphocytes, "B7/BB1," may play a pivotal role in T-cell activation through regulation of their cytokine gene transcription. [See Koulova et al. "The CD28 Ligand B7/BB1 Provides Costimulatory Signal for Alloactivation of CD4+ TCells," J. Exp. Med 173:759 (1991), Gross et al. "Identification and Distribution of the Costimulatory receptor CD28 in the Mouse," J. Immun 149:380 (1992), and Larsen et al. "Functional Expression of the Costimulatory Molecule B7/BB1, on Murine Dendritic Cell Populations," J. Exp. Med 176:1215 (1992)].

While purified B7/BB1 may be a viable T-cell stimulator, it is a complex protein of high molecular weight, and can only be produced in large quantities through recombinant DNA techniques. It is clear that there would be a usefulness for a simpler costimulator that can be synthesized chemically.

SUMMARY OF THE INVENTION

The present invention relates to cyclosporin derivatives to be used as agents for increasing human white blood cell activity and proliferation. In one embodiment, the present invention relates to modified cyclosporin derivatives which have the property of both being non-immunosuppressive and being immunostimulatory agents, i.e., agents useful for increasing lymphocyte proliferation and activity in vitro.

A cyclosporin "derivative" or "analog" has the fundamental structure of Cyclosporin A, namely a cyclic undecapeptide, with amino acid substitutions at particular positions. In accordance with the present invention, a member from the class of novel cyclosporin derivatives is to be mixed with lymphocytes along with one or more antigens. In one embodiment, the member is a cyclosporin derivative modified in either the 1, 4, or 6 position or any combination thereof, by chemical, enzymatic, or biological means.

An analog is "immunostimulatory" if it causes immune cells (e.g., lymphocytes) to be stimulated (e.g., as measured by proliferation). A "costimulatory" is therefore immunostimulatory.

In one embodiment, the present invention contemplates an immunostimulatory analog of the cyclosporin of FIG. 1. In a preferred embodiment, the present invention contemplates the analog having the structure shown in FIG. 3.

It is not intended that the solid phase synthesis be limited to any particular solid particle. In one embodiment, the particle is insoluble in all the solvents which are used and has a stable physical form which permits ready filtration. It also contains a functional group to which the first protected amino acid can be firmly linked by a covalent bond. Many polymers and modes of attachment are possible. Among the possible polymers, the present invention contemplates cellulose, polyvinyl alcohol, polymethacrylate and sulfonated polystyrene. The preferred polymer is methylbenzhydrylamine (MBHA) polystyrene resin.

The present invention contemplates a method of stimulating immune cells, comprising contacting said immune cells in vitro with an immunostimulatory analog of the cyclosporin of FIG. 1. In one embodiment, the method further comprises the step of pretreating the immune cells with a mitogen (e.g., PHA). It is not intended that the present invention be limited by the nature of the immune cells. In one embodiment, the immune cells are lymphocytes.

DESCRIPTION OF THE INVENTION

The present invention relates to cyclosporin derivatives to be used as agents for increasing human white blood cell activity and proliferation.

The description of the present invention involves: (I) Properties of Unmodified Cyclosporin (Prior Art); (II) Properties of Previously Modified Cyclosporin Analogs (Prior Art); (III) Properties of Modified Cyclosporin Analogs of the Present Invention; and (IV) Synthesis of Novel Cyclosporin Analogs.

I. Properties of Unmodified Cyclosporin

Cyclosporin A (CsA) was first discovered in 1970 by researchers at Sandoz Inc. as a metabolite of two strains of fungi: *Tolypocladium inflatum* and *Cylindrocarpon lucidum*. Its strong in vivo immunosuppressive effects were first discovered in trials using mice which led to successful clinical trials, and it is now routinely used to suppress the immune response for procedures such as organ transplantation. One of the attractive properties of cyclosporin A is that, unlike other previous immunosuppressive drugs, it does not show a general inhibition of cell proliferation. Only lymphocytes are inhibited, and the drug is not cytotoxic to those lymphocytes.

Figure 1:
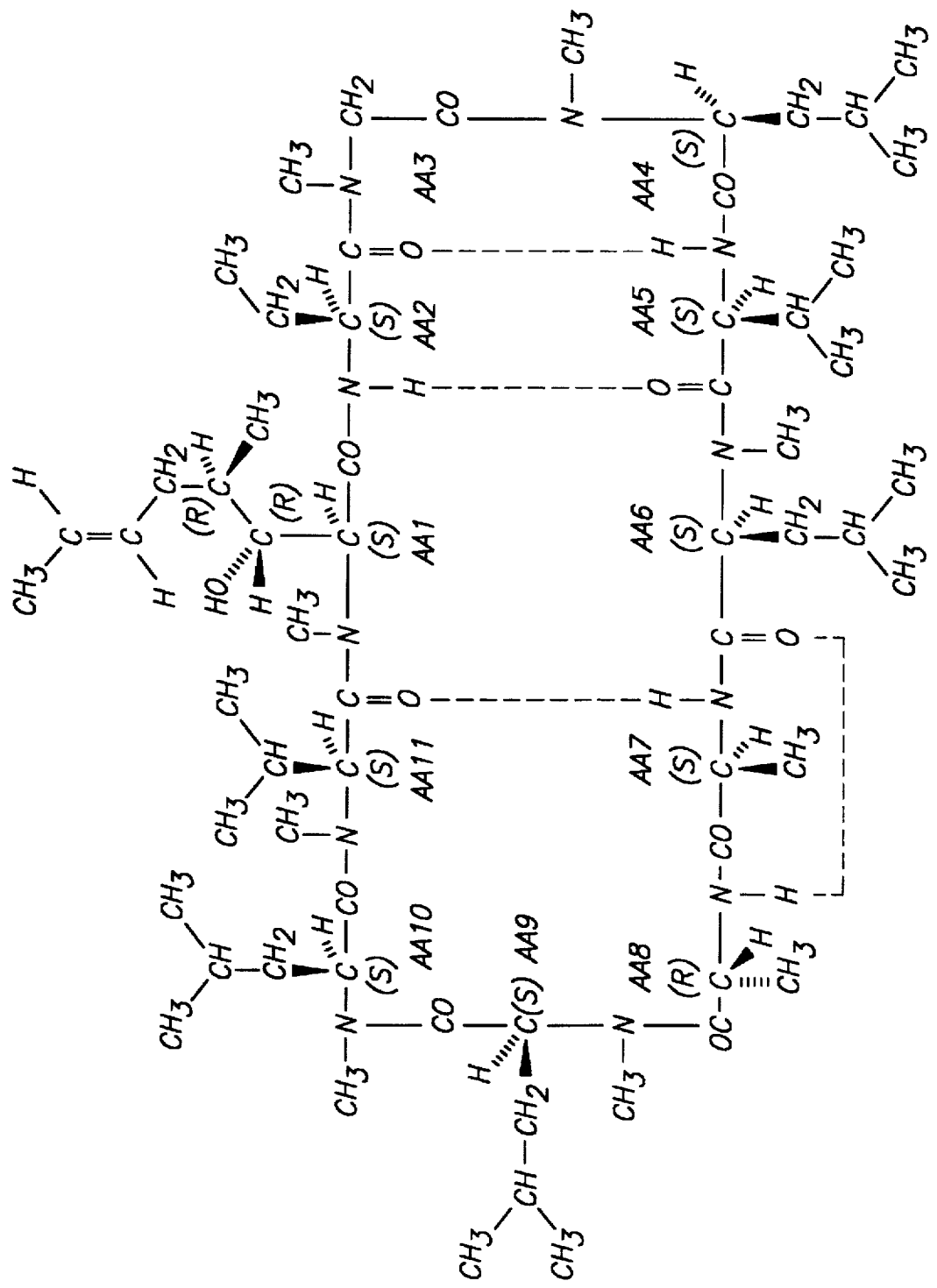
FIG. 1 is a structure of unmodified Cyclosporin A.
Figure 2:
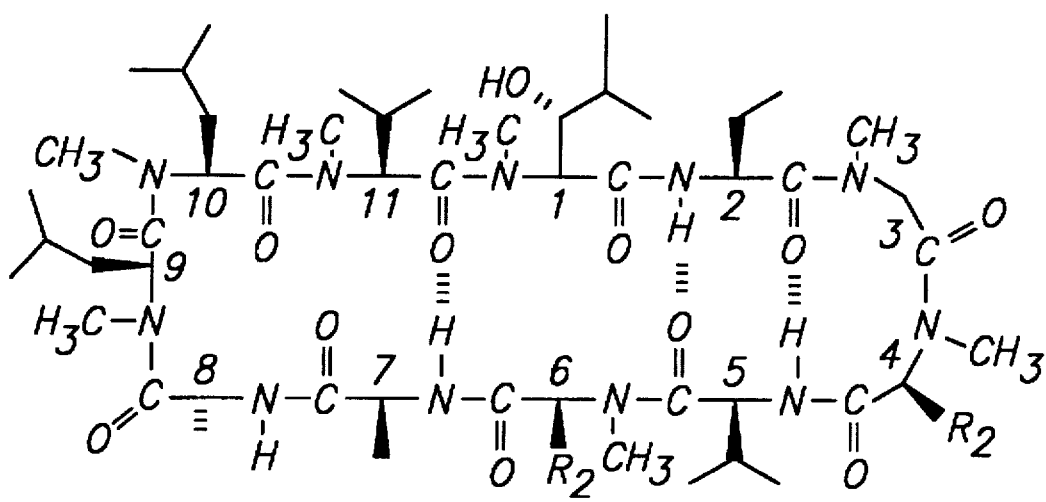
FIG. 2 shows the structure of a previously modified Cyclosporin of the prior art.

A strongly hydrophobic undecapeptide (see FIG. 1), CsA suppresses both humoral and cell-mediated immunity. It is generally believed today that CsA inhibits a relatively early step of lymphocyte proliferation, before the initiation of DNA synthesis, and does not inhibit the cytotoxicity or response of T or B cells which have been already primed to Interleukin-2. The precise mode of action of CsA has not been fully elucidated as of present but it is agreed upon that: 1) CsA binds mainly to cyclophilin, an abundant cytoplasmic protein, in the cell; 2) CsA affects internal cell $Ca^{2+}$ sensitivity; and 3) a combination of these properties as well as other unknown steps may lead to reduced production of Interleukins and other cytokines in the cell, which would lead to decreased lymphocyte activation and proliferation. (See *Cyclosporin, Mode of Action and Clinical Application*, Thomson: Kluwer Academic Publishers, 1989; *Cyclosporine, Biological Activity and Clinical Applications*, Kahan: Elsevier Biomedical Press, 1982; and *Cyclosporin A*, White: Grune & Stratton, 1984).

In addition to its clear and tested utility as an immunosuppressive agent, it was recently discovered (and subsequently patented) by Andrieu that CsA does possess potential utility as an anti-AIDS agent, i.e., that is has been shown to reduce the reproduction of the HIV virus. (See U.S. Pat. No. 4,814,323).

II. Properties of Previously Modified Cyclosporin Analogs

There have also been numerous studies of the biological and medicinal effects of modified cyclosporin derivatives.

Many of these cyclosporin derivatives have possessed novel properties and have in fact been patented. The convention for cyclosporin analog nomenclature includes listing any modified amino acids and their positions relative to unmodified cyclosporin A. For example, an analog of cyclosporin possessing Serine in place of the normal Valine as the fifth amino acid would have the name (Ser$^5$)-CsA.

CsA analogs have been previously synthesized. The biological activity of these analogs ranges from immunosuppressive properties equal to that of modified CsA to having reduced or even no immunosuppressive activity. Another novel class of CsA derivatives was disclosed by the present inventor in 1986. [See Rich, D., Dhaon, M., Dunlap, B. and Miller, S., J. Med. Chem. 29:978 (1986)]. These CsA analogs all contained modified amino acids in the 1 position. In addition there have been several patented CsA derivatives developed by Sandoz, including (Allylgly$^2$)-CsA, ([D]-Ser$^8$)-CsA, and (O-(2-hydroxyethyl)(D)Ser$^8$)-CsA which possess strong immunosuppressive, anti-inflammatory, and antiparasitic activity. (See U.S. Pat. Nos. 4,384,996, 4,771,122 and 5,284,826).

Recently, however, there has been added emphasis on discovering CsA analogs which possess little or no immunosuppressive activity, for their utility, not as immunosuppresssive agents, but as anti-AIDS agents. As discussed supra, a recently issued patent described the use of unmodified CsA to combat the spread of the HIV virus. Clearly it would be preferable to use a compound to treat AIDS which could inactivate the HIV virus, while not suppressing the immune system, as CsA does. Such reasoning has led researchers to investigate CsA analogs with both such properties. A European Patent (# 0484281A2) again by Sandoz, discloses CsA derivatives which indeed are active against HIV replication, but lack immunosuppressive activity.

III. Properties of Cyclosporin Analogs of the Present Invention

Figure 3:
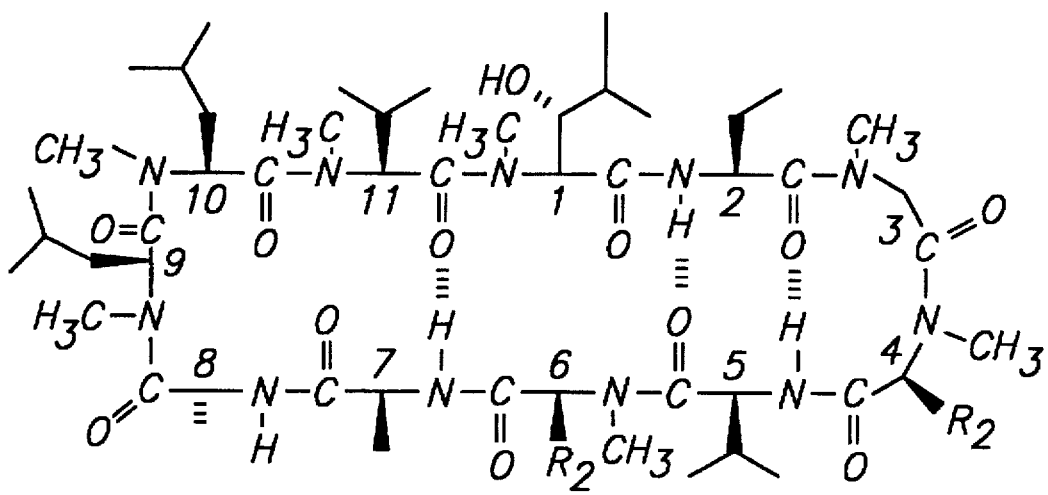
FIG. 3 shows the structure of a preferred Cyclosporin analog of the present invention.

During the course of preparing novel CsA analogs, it was discovered that immunostimulatory analogs of CsA could also be synthesized. In particular, the [MeLeu(3-OH)$^1$, MeAla$^{4,6}$]CsA (FIG. 3) and the [(D)-MeVal$^{11}$, MeLeu(3-OH)$^1$]CsA analogs augmented the mitogen induced in vitro DNA synthesis response of human peripheral blood monocytes (PBMCs) (see Tables 5–6) at all the concentrations tested (e.g., 0.001 μg/ml to 10 μg/ml).

This novel property has not been previously described for any cyclosporin analog. As CsA is known primarily as an immunosuppressive agent, finding a derivative of CsA which possessed the opposite effect was totally unexpected.

IV. Synthesis of Cyclosporin Analogs of the Present Invention

The present invention relates to the synthesis of CsA analogs with amino acid substitutions either the 1, 4, or 6, positions, or any combination thereof. These analogs were tested based on two criteria: 1) their ability to act as immunostimulatory agents; and 2) their ability to inhibit cytopathic effect due to infection by the HIV virus. It was found that two analogs, [D-MeVal$^{11}$, L-MeLeu(3-OH)$^1$]-CsA and [MeLeu(3-OH)$^1$, MeAla$^{4,6}$]-CsA, were able to function as immunostimulatory agents as shown by their ability to augment the PHA-induced DNA synthetic response of PBMCs. In addition the latter analog was able to inhibit the cytopathic effect due to infection by the HIV virus, therefore giving it potential utility as an anti-AIDS therapeutic.

This preferred analog of the present invention was synthesized according to the following general procedure:

First, the novel amino acid L-MeLeu(3-OH) was synthesized (described later) and subsequently condensed with acetone into a modified form.

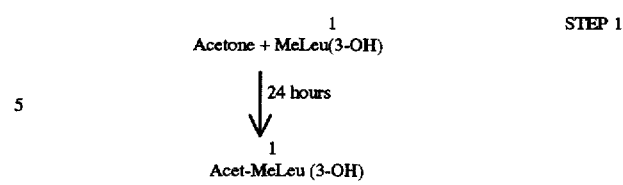

Second, a methylalanine amino acid (MeAla), N-protected by a t-butoxycarbonyl group (Boc), was reacted with an alanine amino acid (Ala), C-protected by a benzyl ester group (OBzl), along with (bis(2-oxo-3-oxazolidinyl) phosphonic chloride) (BOP-Cl) and diisopropylethylamine (DIEA) to form an N and C-protected MeAla-Ala dipeptide.

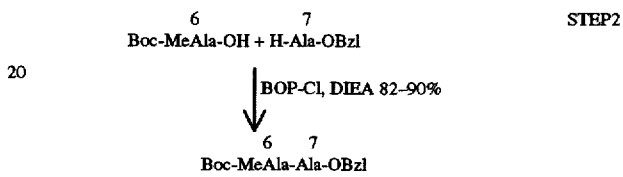

Third, the N and C-protected MeAla-Ala dipeptide was N-deprotected by reaction with trifluoroacetic acid (TFA).

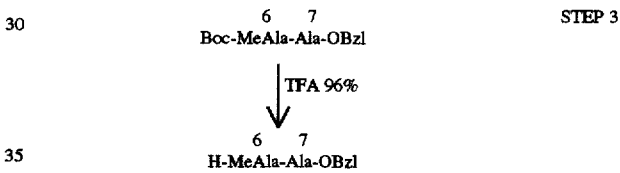

Fourth, the C-protected MeAla-Ala dipeptide was reacted with a valine amino acid (Val), N-protected by Boc, along with BOP-Cl and DIEA to form an N and C-protected Val-MeAla-Ala tripeptide.

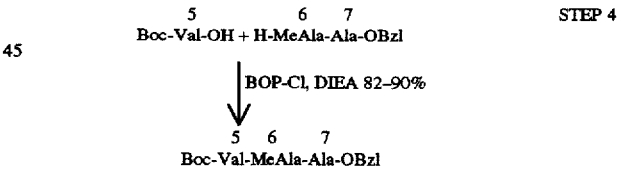

Fifth, the N and C-protected Val-MeAla-Ala tripeptide was N-deprotected by reaction with TFA.

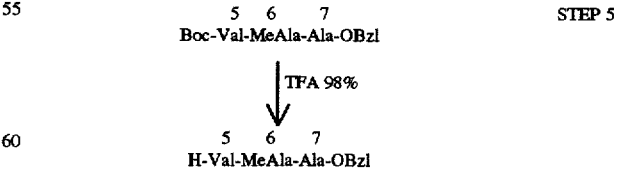

Sixth, the C-protected Val-MeAla-Ala tripeptide was reacted with a MeAla amino acid, N-protected by Boc, along with BOP-Cl and DIEA to form an N and C-protected MeAla-Val-MeAla-Ala tetrapeptide (SEQ ID NO:3).

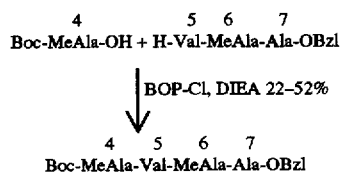

Seventh, the N and C-protected MeAla-Val-MeAla-Ala (SEQ ID NO:3) tetrapeptide was N-deprotected by reaction with TFA.

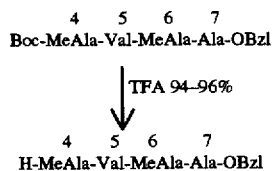

Eighth, the C-protected MeAla-Val-MeAla-Ala (SEQ ID NOS:3) tetrapeptide was reacted with an a-aminobutyric acid-sarcosine dipeptide (Abu-Sar), N-protected by Boc, along with BOP-Cl and DIEA to form an N and C-protected Abu-Sar-MeAla-Val-MeAla-Ala hexapeptide (SEQ ID NO:4).

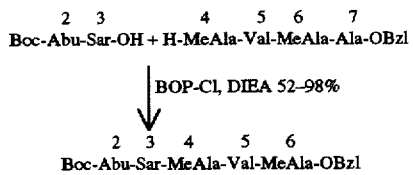

Ninth, the N and C-protected Abu-Sar-MeAla-Val-MeAla-Ala hexapeptide (SEQ ID NO:4) was N-deprotected by reaction with TFA.

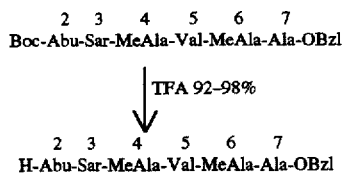

Tenth, the C-protected Abu-Sar-MeAla-Val-MeAla-Ala hexapeptide (SEQ ID NO:4) was reacted with the modified MeLeu(3-OH) amino acid of the first step along with 1-hydroxybenzotriazole (HOBt), N-methyl morpholine (NMM), and dicyclohexyl carbodiimide (DCC) to form an N and C-protected MeLeu(3-OH)-Abu-Sar-MeAla-Val-MeAla-Ala heptapeptide (SEQ ID NO:4).

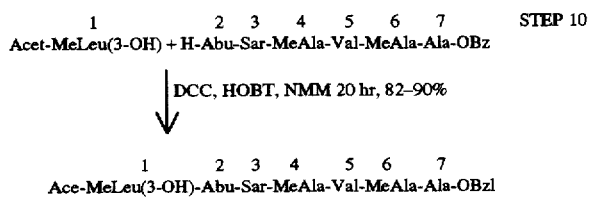

Eleventh, the N and C-protected heptapeptide (SEQ ID NO:5) was N-deprotected by reaction with aqueous hydrochloric acid and methanol.

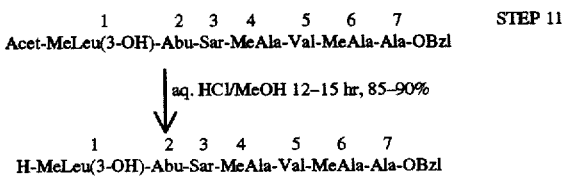

Twelfth, a methylvaline amino acid (MeVal), C-protected by a Boc group was reacted with a methylleucine amino acid (MeLeu), N-protected by a Cbz group, along with BOP-Cl and DIEA to form an N and C-protected MeLeu-MeVal dipeptide.

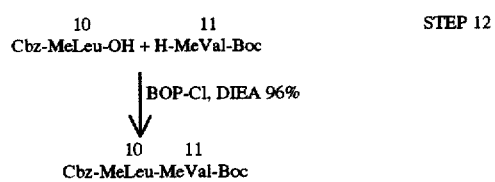

Thirteenth, the N and C-protected dipeptide was N-deprotected by catalytic hydrogenation.

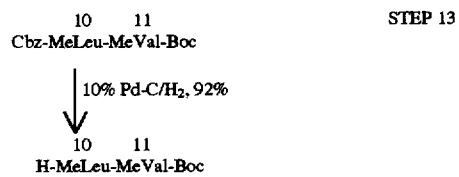

Fourteenth, the C-protected dipeptide was reacted with a methylleucine amino acid (MeLeu), N-protected by a Cbz group, along with BOP-Cl and DIEA to form an N and C-protected MeLeu-MeLeu-MeVal tripeptide.

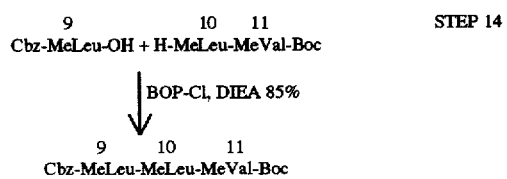

Fifteenth, the N and C-protected tripeptide was N-deprotected by catalytic hydrogenation.

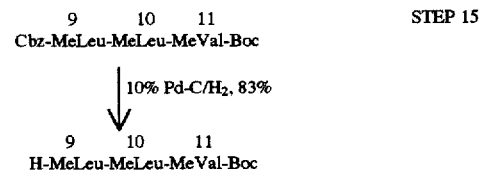

Sixteenth, the C-protected tripeptide was reacted with a D-alanine amino acid, N-protected by an Fmoc group, along with BOP-Cl and DIEA to form an N and C-protected D-Ala-MeLeu-MeLeu-MeVal tetrapeptide (SEQ ID NO:2).

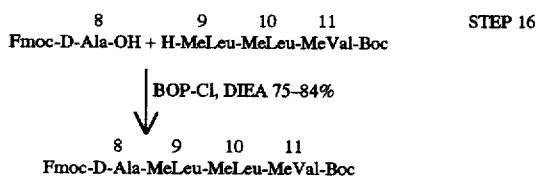

Seventeenth, the N and C-protected tetrapeptide (SEQ ID NO:2) was C-deprotected by reaction with trifluroacetic acid.

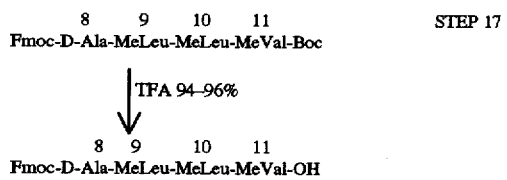

Eighteenth, the C-protected heptapeptide (SEQ ID NO:5) from the eleventh step was reacted with the (D)-alanine-methylleucine-methylleucine-methylvaline tetrapeptide (SEQ ID NO:2) (D-Ala-MeLeu-MeLeu-MeVal) from the seventeenth step, N-protected by 9-fluorenylmethoxycarbonyl (Fmoc), along with BOP-Cl and NMM to form an N and C-protected D-Ala-MeLeu-MeLeu-MeVal-MeLeu(3-OH)-Abu-Sar-MeAla-Val-MeAla-Ala undecapeptide (SEQ ID NO:6).

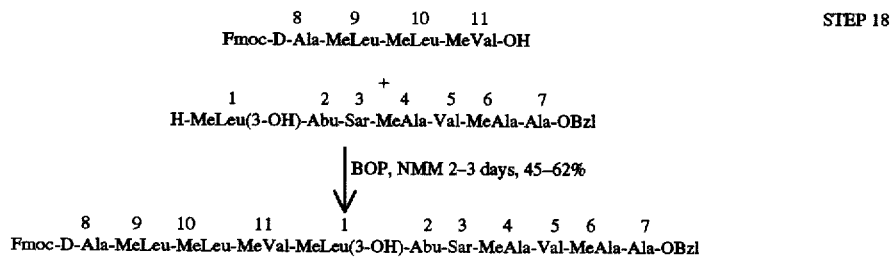

Nineteenth, the N and C-protected D-Ala-MeLeu-MeLeu-MeVal-MeLeu(3-OH)-Abu-Sar-MeAla-Val-MeAla-Ala undecapeptide (SEQ ID NO:6) was cyclized by reaction with to aqueous sodium hydroxide, ethanol, 4-dimethylaminopyridine (DMAP) and propyl-phosphonic arthydride (Pr-PO$_2$)$_3$ to form the cyclosporin analog (SEQ ID NO:21).

EXPERIMENTAL

The following examples serve to illustrate certain preferred embodiments and aspects of the present invention and are not to be construed as limiting the scope thereof.

In the experimental disclosure which follows, the following abbreviations apply: MeBmt ([(4R)-N-methyl-4-butenyl-4-methyl-L-threonine]; Abu (a-aminobutyric acid); MeLeu(3-OH) (3-hydroxy-N-methylleucine); Sar (sarcosine); MeAla (N-methylalanine); Gly (glycine); Ala (alanine); Val (valine); Leu (leucine); Ile (isoleucine); Met (methionine); Pro (proline); Phe (phenylalanine); Trp (tryptophan); Ser (serine); Thr (threonine); Cys (cysteine); Tyr (tyrosine); Asp (asparagine); Gln (glutamine); Asp (aspartic acid); Glu (glutamic acid); Lys (lysine); Arg (arginine); His (histidine); Fmoc (9-fluorenylmethoxycarbonyl); HOBt (1-hydroxybenzotriazole); BOP-Cl (bis(2-oxo-3-oxazolidinyl)phosphonic chloride); NMM (N-methyl morpholine); DCU (dicyclourea); DIEA (diisopropylethylamine); DCC (dicyclohexyl carbodiimide); DMAP (4-dimethylaminopyridine); (Pr-PO$_2$)$_3$ (propyl-phosphonic anhydride); TFA (trifluoroacetic acid); OBzl (benzyl ester); PyBroP (bromotripyrrolidino-phosphonium hexafluorophosphate); EtOAc (ethyl acetate); DIPCDI (diisopropylcarbodiimide); HATU [O-(7-azabenzotriazol-1-yl)-1,1,2,2,-tetramethyluronium hexafluorophosphate]; NMR (Nuclear Magnetic Resonance Spectroscopy); FABMS (Fast Atom Bombardment Mass Spectrometry); hsp70 (Heat Shock Protein); MeVal (N-methylvaline); Boc (t-butoxycarbonyl); DMF (dimethylformamide); THF (tetrahydrofuran); MeLeu (N-methylleucine); MeOH (methanol); PHA (phytohemagglutinin).

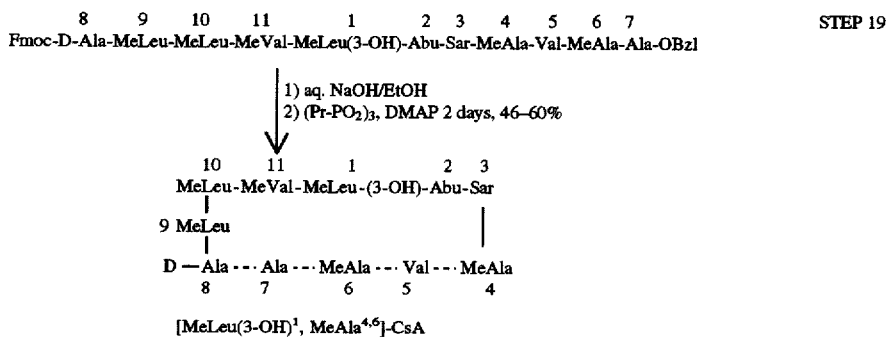

Example 1

Synthesis of CsA Analogs

The total synthesis of CsA was first reported by Wenger [Helv. Chim. Acta. 67:501 (1984)] (discussed supra). The strategy followed route in which CsA was built up in the direction of the arrows in FIG. 4. The point of cyclization was chosen at the peptide bond between the Ala[7] and (D)-Ala[8] for the following two reasons: 1) both amino acids are without an N-methyl group, which presents an easier bond formation as compared to N-methyl amino acids; 2) intramolecular H-bonds might be present in the linear undecapeptide, which stabilize the linear undecapeptide in a folded conformation and thus facilitating ring closure. For the synthesis of the linear undecapeptide, a technique of fragment coupling between the tetrapeptide (residues 8–11) (SEQ ID NO:2) and the heptapeptide (residues 1–7) (SEQ ID NO:10) was chosen. The heptapeptide fragment (SEQ ID NO:10) was prepared by a fragment coupling of the dipeptide (residues 2–3) and the tetrapeptide (residues 4–7) (SEQ ID NO:22), followed by introducing the amino acid MeBmt at the end of the synthesis (note that in the preferred analog this amino acid was replaced by the novel amino acid MeLeu(3-OH)). This sequence had two obvious advantages: 1) fragment coupling onto the sarcosine (residue 3) prevented the possibility of racemization; 2) the number of steps after the introduction of the precious 1-position amino acid was minimized. The undecapeptide could be cyclized to CsA after removal of N- and C-terminal protecting groups.

Figure 9:
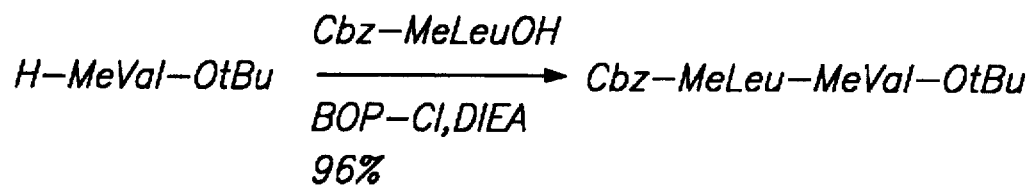
FIG. 9 shows the synthesis of [MeLeu(3-OH)$^1$]CsA Analogs (SEQ ID NO:2).
Figure 9:
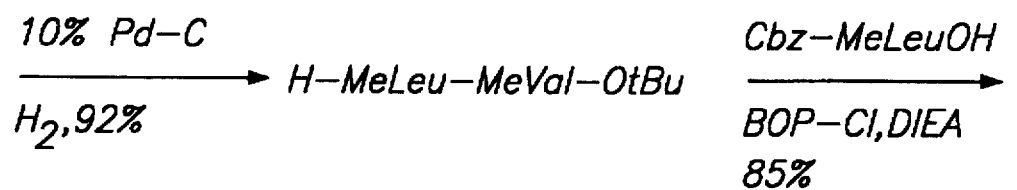
Figure 9:
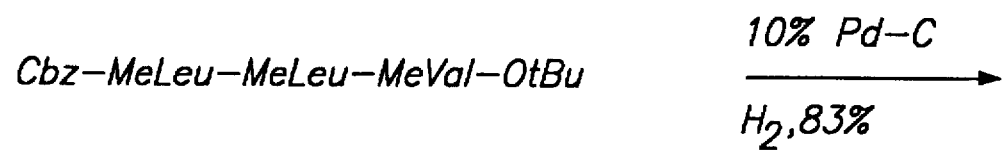
Figure 9:
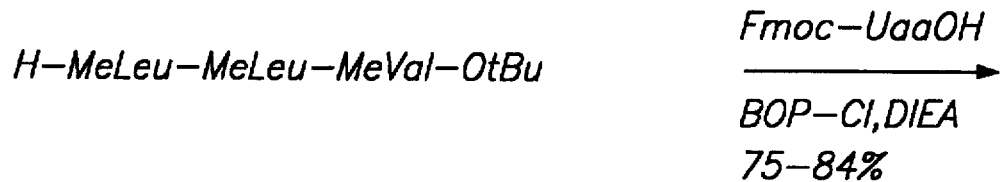
Figure 9:
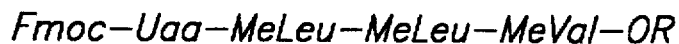
Figure 9:
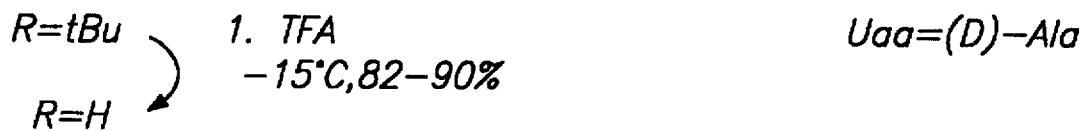
Figure 10:
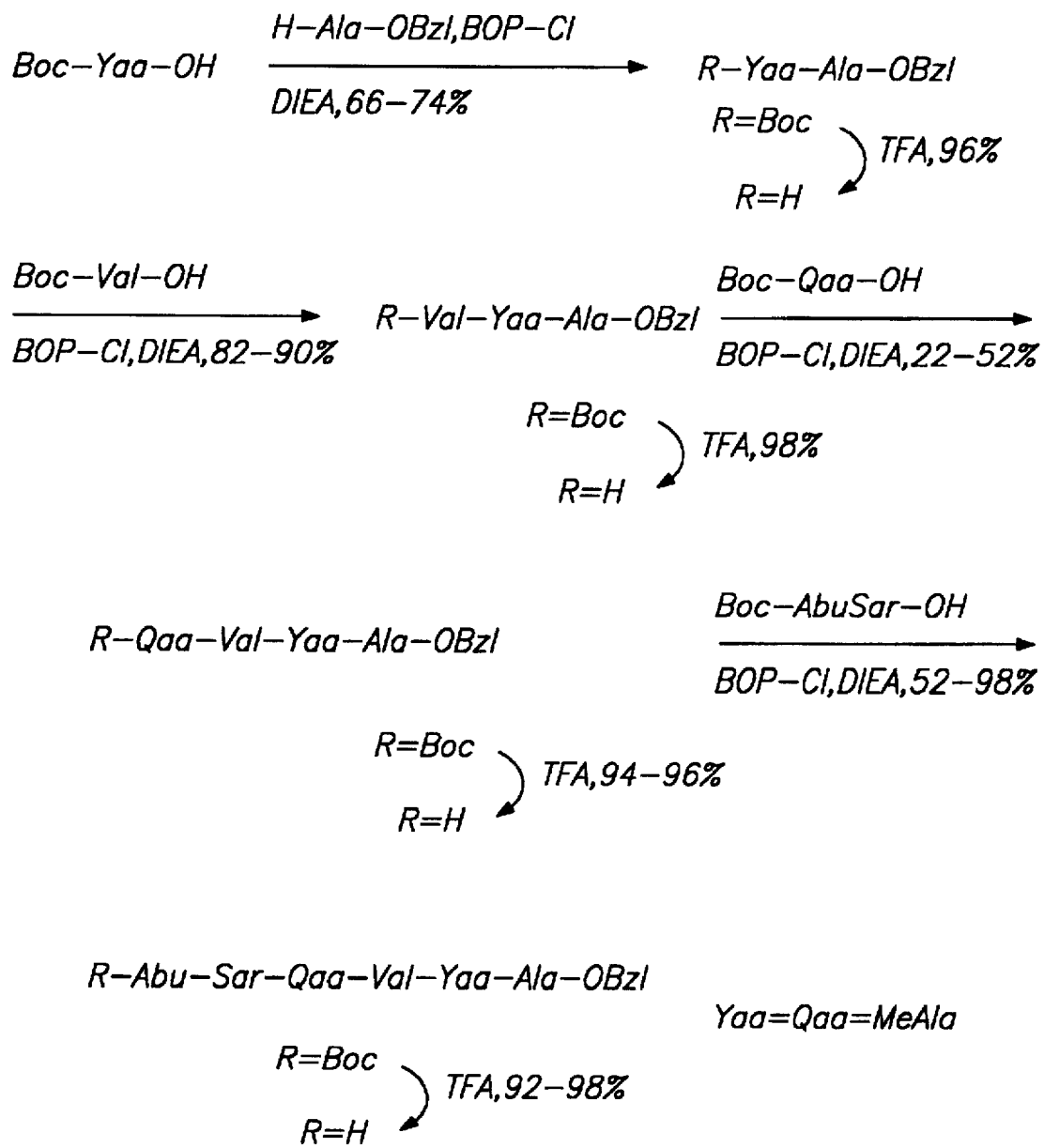
FIG. 10 shows the synthesis of CsA 2–7 analogous fragments (SEQ ID NOS:3 and 4).
Figure 11:
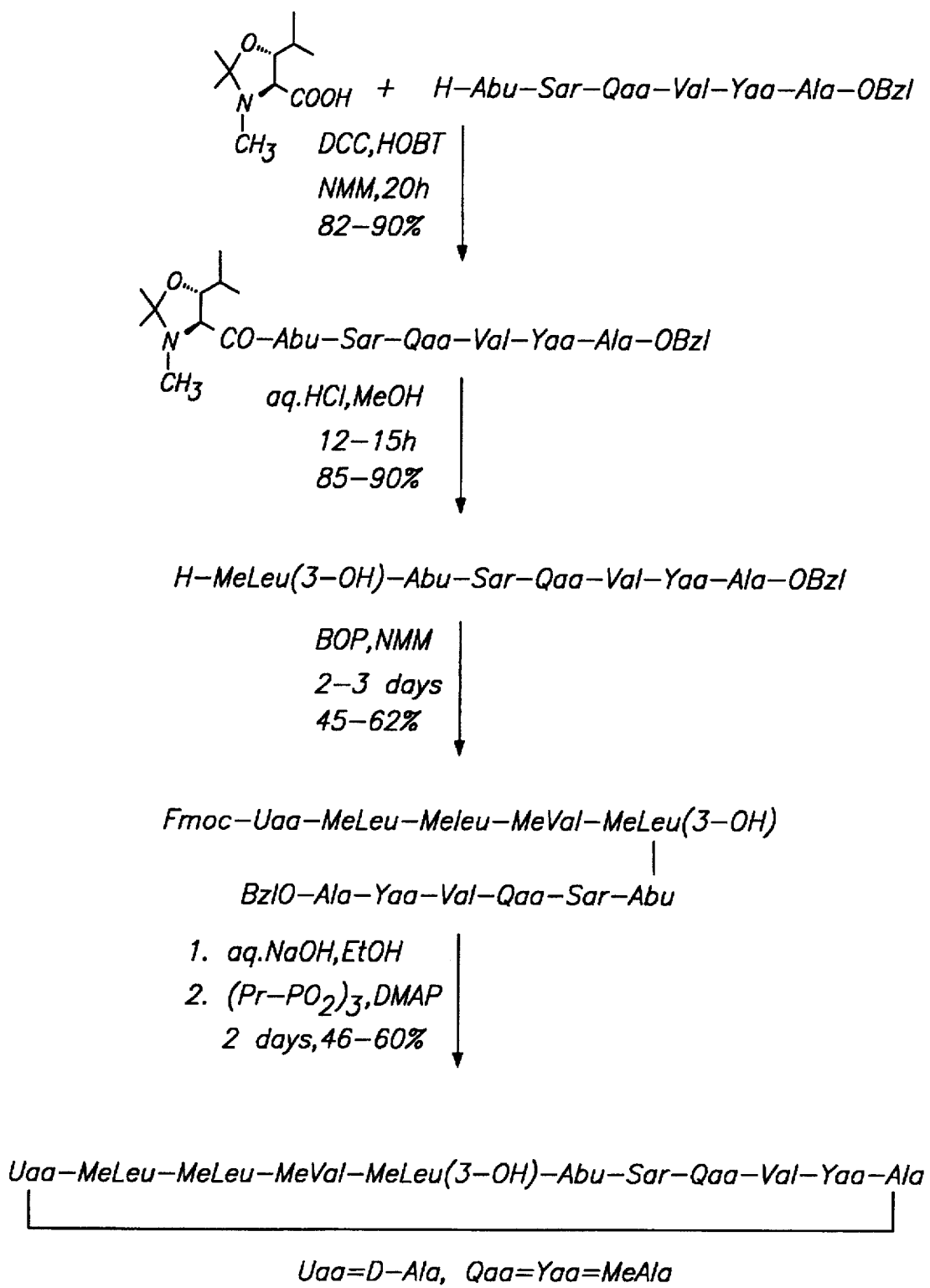
FIG. 11 shows the synthesis of CsA 8–11 analogous fragments (SEQ ID NOS:4–7).

The synthesis of [MeLeu(3-OH)[1]]CsA analogs modified at residues 3–8 was carried out as originally described. [See Colucci, W. J., Tung, R. D., Petri, J. A. and Rich, D. H., J. Org. Chem. 55:2895 (1990)]. The CsA 2–7 tetrapeptides were constructed starting from H-Ala-OBzl and adding the appropriate amino acids step by step in a series of coupling-deprotection procedures (FIG. 10) (SEQ ID NOS:3 and 4). After deprotection of N-terminal Boc group, the resultant tetrapeptides were condensed with Boc-AbuSar-OH using the BOP-Cl/DIEA method to provide the hexapeptides. After removal of the N-Boc group with TFA, the corresponding amino-hexapeptides were obtained and quickly used for further reactions. The optical rotations and yields of the peptide fragments for BOP-Cl mediated couplings and N-deprotections are summarized in Table 1 and Table 2 (SEQ ID NOS:22–26). The available hexapeptides were then acylated with the acetonide-protected MeLeu(3-OH) using DCC/HOBt method to give desired protected heptapeptides (82–90%) as shown in FIG. 9 (SEQ ID NO:2). These heptapeptides appear as two major conformers in CDCl$_3$ by NMR due to the N-methyl amide conformers. Removal of the acetonide protecting group of the heptapeptides was performed using 1M HCl in methanol for 15 hours. The resultant amino-heptapeptides were purified by flash chromatography (85–90%). The CsA 8–11 tetrapeptides were constructed starting from H-MeVal-Boc and adding the appropriate amino acids step by step in a series of coupling-deprotection procedures (FIG. 11). [For a more detailed procedure see Tung, R. D., Dhaon, M. K. and Rich, D. H., J. Org. Chem. 51:3350 (1986)]. For the coupling of the CsA 8–11 tetrapeptides and heptapeptides, Castro's BOP-Cl reagent and N-methyl morpholine were employed to achieve these linkages. The resultant undecapeptides were obtained usually in relatively low yields 45–62% as compared to the 73% reported by Wenger in the case of CsA synthesis. [See Wenger, R. M. Helv. Chim. Acta. 67:501 (1984)].

Figure 12:
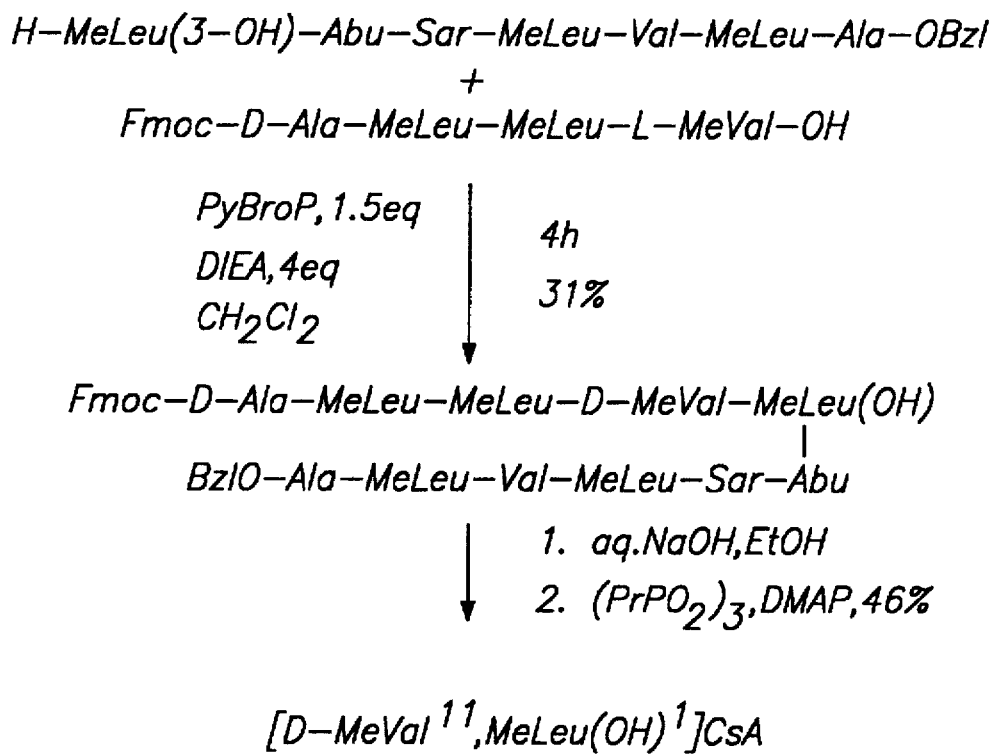
FIG. 12 shows the PyBroP Mediated 4+7 coupling reaction (SEQ ID NOS:2, 8, 9).

Recently, a type of pyrrolidinophosphonium complexes abbreviated as PyBroP (bromotripyrrolidino-phosphonium hexafluorophosphate), PyCloP, and PyBoP were reported as coupling reagents for peptide synthesis. [See Coste, J., Frerot, E., Jouin, P. and Castro, B., Tetrahedron Lett. 32:1967 (1991)]. According to Castro's report, N-methyl amino acids could be coupled efficiently by using PyBroP/DIEA. Because of the low yield for the 4+7 coupling for the synthesis of undecapeptides, it was attempted to use PyBroP (1.5 equiv) in the coupling of the tetrapeptide (1.5 equiv) and the heptapeptide in the presence of DIEA (4 equiv) as shown in FIG. 12.

As expected, PyBroP did drive the coupling reaction to completion in 4 hours. However, PyBroP also gave multiple spots by TLC and did not improve the yield of product (only 32%). The unexpected result was that the epimerized undecapeptide (with (D)-configuration at residue MeVal) was obtained as the major product. Racemization was presumably due to the formation of hydrobromide during the activation of the carboxylic group of tetrapeptide with PyBroP, which could cause C-terminal residue [MeVal[11]] to epimerize. [The Peptides: Analysis, Synthesis, Biology (Vol. 1) Academic Press Inc. (1979)].

Figure 13:
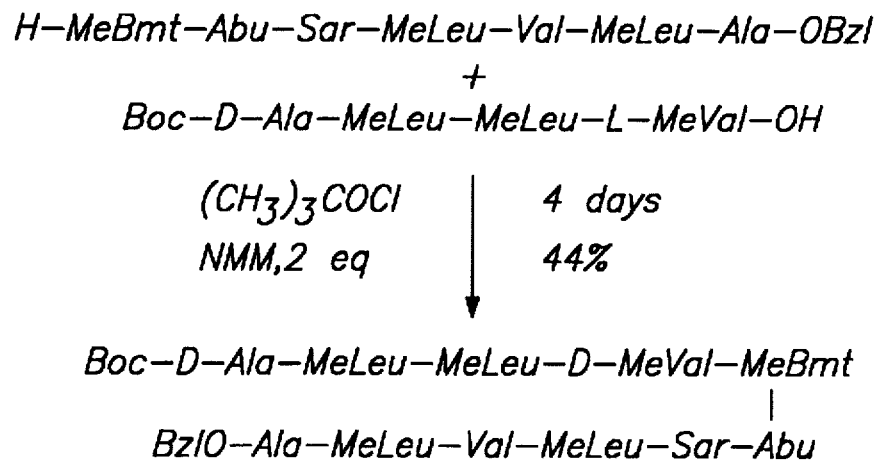
FIG. 13 shows inverted conversion in 4+7 coupling as reported by Wenger [Helv. Chim. Acta. 67:501 (1984)] (SEQ ID NOS:12–25).

A similar result has been reported by Wenger (discussed supra) (see FIG. 13), in which the mixed pivalic anhydride method (using pivaloyl chloride/N-methylmorpholine), gave the configuration-inverted (at MeVal) undecapeptide (SEQ ID NO:11) Boc-(D)-Ala-MeLeu-MeLeu-(D)-MeVal-MeBmt-Abu-Sar-MeLeu-Val-MeLeu-Ala-OBzl when coupling the tetrapeptide (SEQ ID NO:2) Boc-(D)-Ala-MeLeu-MeLeu-L-MeVal-OH with the corresponding heptapeptide. In both cases, epimerization may be due to high halide concentrations in the reaction media.

Although it took 3 days to complete the coupling reaction, the BOP-Cl reagent is still preferable for the 4+7 fragment coupling in the synthesis of CsA analogs, since racemization of MeVal is minimized. In order to complete the final cyclization, the N-Fmoc and C-Bzl protecting groups of the undecapeptides were removed simultaneously by reaction with 0.2N of aqueous NaOH in ethanol for 5–12 hours. (See FIG. 11 ). After workup, the crude, fully-deprotected undecapeptides (SEQ ID NOS:5–7) were cyclized, using propylphosphonic anhydride (1.5 equiv) and DMAP (6 equiv), in a dilute solution (~2×10$^{-4}$M) for 2 days to give CsA analogs in 37–60% yields.

The physical properties of these CsA analogs and their linear undecapeptide intermediates are summarized in Table 3.

Example 2

General Synthetic Procedures General Procedure A: Synthesis of β-Hydroxy-N methylleucine (MeLeu(OH))

Figure 5:
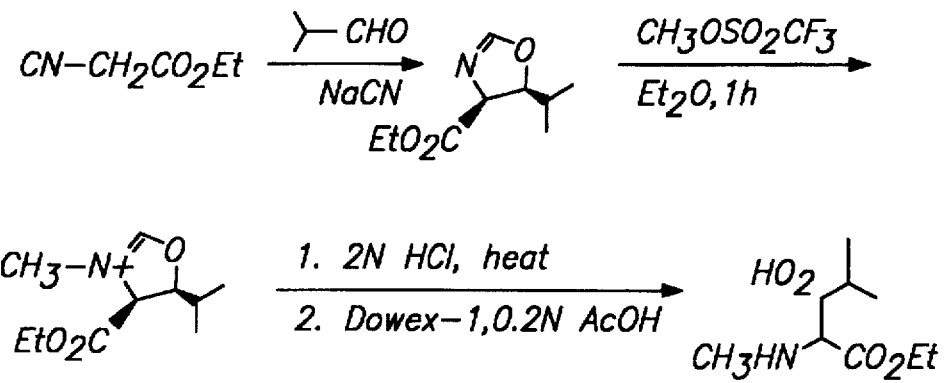
FIG. 5 shows the synthesis of (±)-threo-β-hydroxy-N-methylleucine.

A synthesis scheme for MeLeu(3-OH) has been reported [see Rich, D. H., Dhaon, M. K., Dunlap, B. and Miller, S. P. F, J. Med. Chem. 29:978 (1986)] in which the procedure developed by Schöllkopf [see U. Angew. Chem. Int. Ed. 16:339 (1977)] for the synthesis of β-hydroxy amino acids was employed (FIG. 5). The reaction of isocyanoacetate with isobutyraldehyde in the presence of NaCN gave the thermodynamically stable trans-oxazoline as the major product. The trans-oxazoline was treated with methyl triflate at room temperature to give the N-methyl imidate. Hydrolysis of the N-methyl imidate with dilute HCl followed by ion-exchange chromatography of the amino acid gave (±)-threo-β-hydroxy-N-methylleucine.

Figure 6:
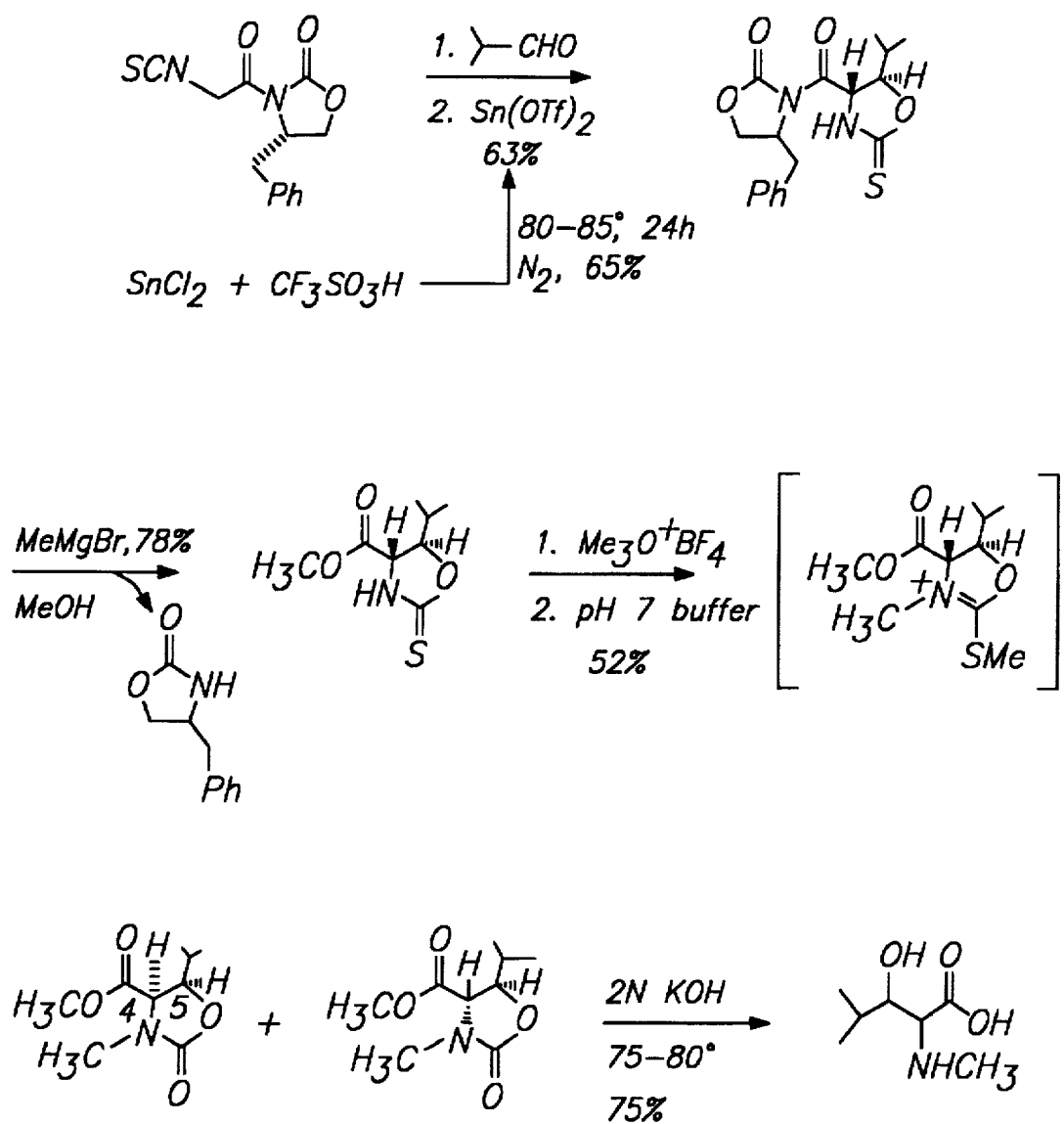
FIG. 6 shows the synthesis of (2S,3R)-3-Hydroxy-N-methylleucine by the Evans method.
Figure 7A:
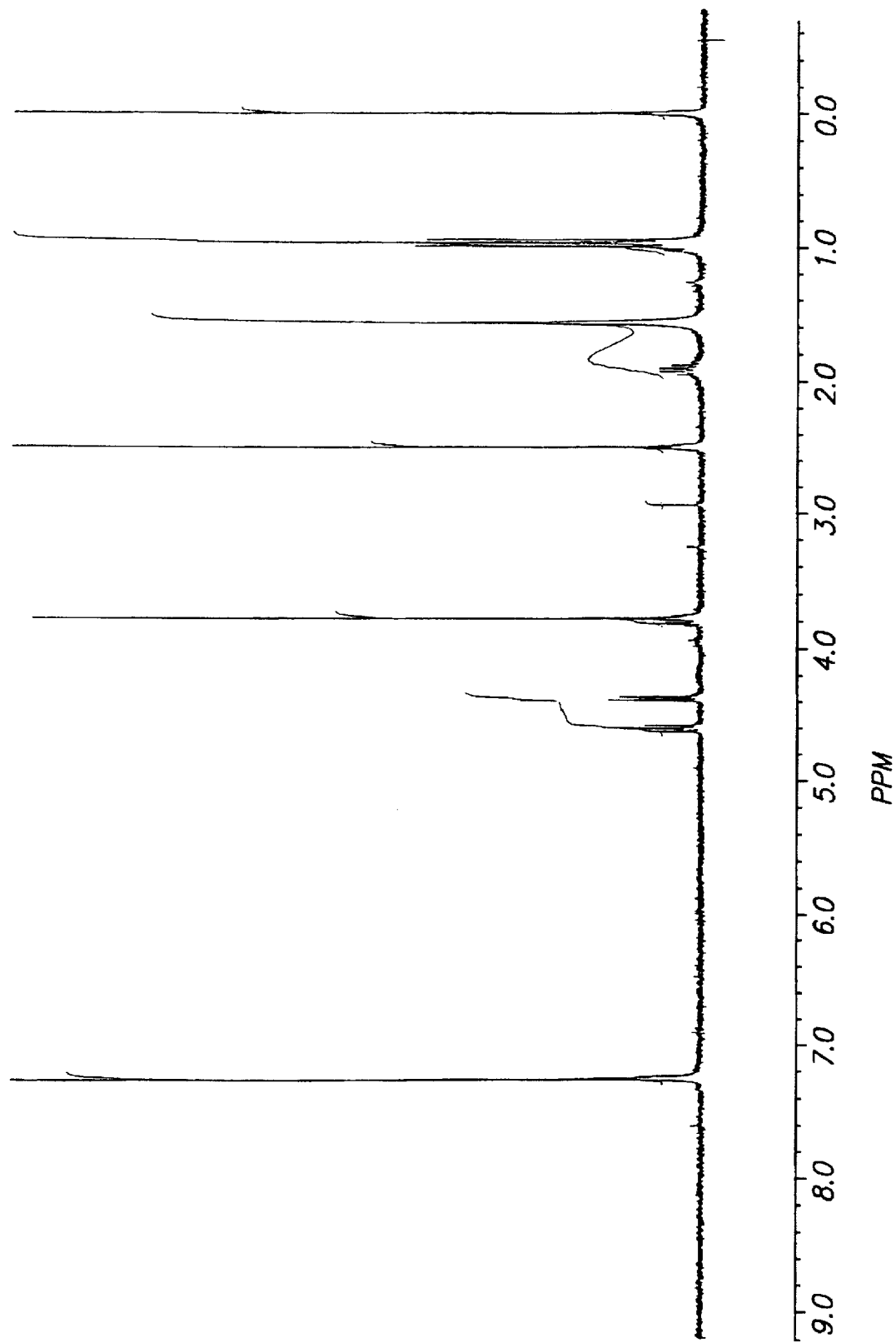
FIG. 7A shows the $^1H$ NMR spectra of one of the oxazolidinone epimers.
Figure 7B:
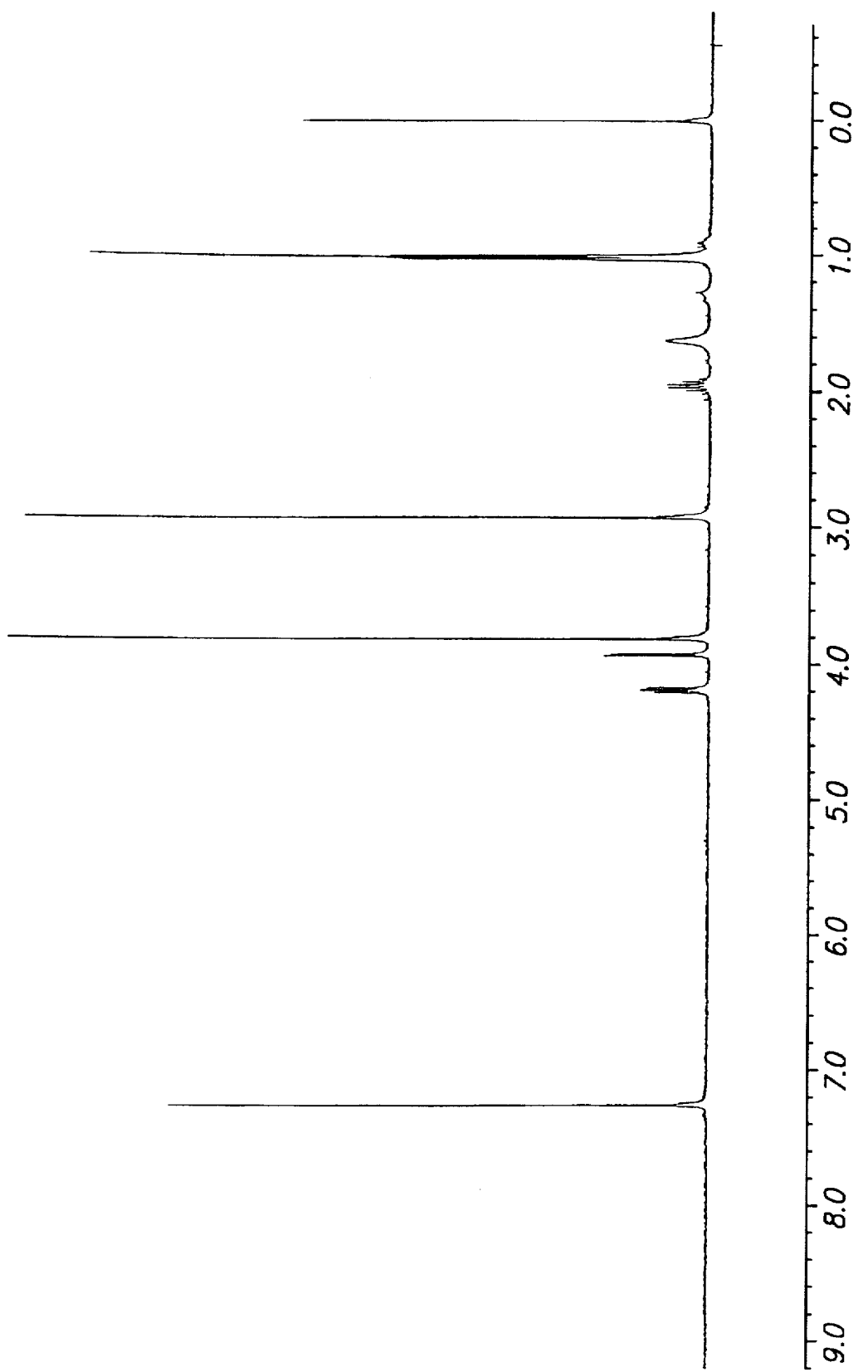
FIG. 7B shows the $^1H$ NMR spectra of the other oxazolidinone epimer.
Figure 8:
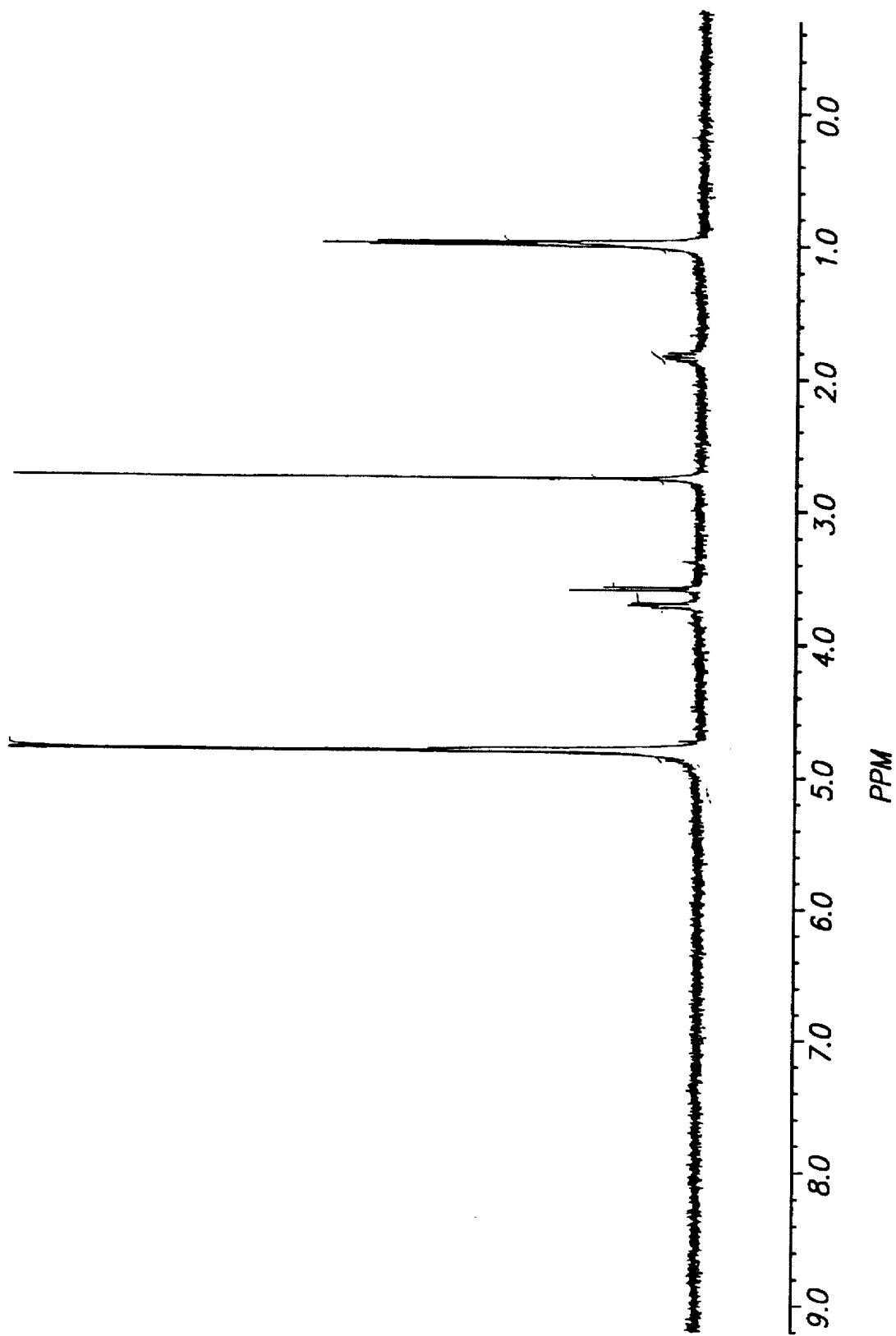
FIG. 8 shows the $^1H$ NMR spectra of β-hydroxy-N-methylleucine.

At the same time, an elegant asymmetric glycine enolate reaction was developed by Evans and Weber for the synthesis of MeBmt and other chiral amino acids. [See Evans, D. A. and Weber, A. E., J. Am. Chem. Soc. 108:6757 (1986)]. The approach was also applied to prepare MeLeu (OH) [see FIG. 6]. In the reaction sequence, the chiral glycine synthon isothiocyanate was obtained from corresponding chloroacetate and followed by azide replacement in 56% yield. The isothiocyanate chiral auxiliary was condensed with isobutyraldehyde under stannous triflate mediated aldol reaction (−78° C. for 4 h) to give the aldol adduct in 63% yield (>90% e.e). Transesterification with a solution of magnesium methoxide in methanol at room temperature for 3 min gave the methyl ester in 78–82% yield. The yield of the bis-methylation was low, 52% as compared to 76% of Evans in MeBmt synthesis. Two epimers are usually obtained in a ratio of 1:5, which was not found by Evans for the MeBmt synthesis. The $^1$H NMR spectra of the epimers were compared as shown in Table 4 and FIG. 7. Hydrolysis of the desired trans-oxazolidinone with 2N KOH under reflux gave the pure β-hydroxy-N-methylleucine (see $^1$H NMR spectra in FIG. 8) after chromatographic purification over Sephadex LH-20.

General Procedure B: Synthesis of CsA Tetrapeptide Fragment 8–11 (SEQ ID NO:2)

A solution of the eleven position amino acid (3.01 g, 13 mmol) in 20 mL of dioxane was reacted with 4.95 g (26 mmol) of p-toluenesulfonic acid monohydrate and heated under reflux for 40 min ($CaCO_3$ drying tube). The mixture was cooled in an ice/water bath, then transferred to a thick walled pressure flask, and treated with 25 mL of isobutylene previously condensed at 78° C. The flask was capped and vigorously stirred at room temperature for 19 hr, chilled and uncapped, and the contents were pored into cold dilute aqueous NaOH. The mixture was adjusted to pH=10 then extracted with ether (2×25 mL). The organic layers were combined, dried and evaporated and the residue was distilled yielding the eleven position amino acid C-protected by Boc.

A solution of the eleven position amino acid C-protected by Boc (2.28 g, 15 mmol) was reacted with 4.19 g (15.1 mmol) of N-protected ten position amino acid in 200 mL of $CH_2Cl_2$ and was cooled with stirring under inert atmosphere in a ice/water bath. The cold mixture was treated with DIEA (5.75 mL, 32.3 mmol) followed by BOP-Cl (4.19 g, 16.5 mmol). The mixture was stirred for 2 hr in the cold and the concentrated in vacuo. The residue was partitioned between water and ethyl acetate and the organic layer was separated and washed with $KHSO_4$, $H_2O$, 1N $NaHCO_3$, 50% brine, and brine. After drying over $Na_2SO_4$ it was concentrated in vacuo to a yellow oil, and purified by flash chromatography on 300 g of silica gel, eluting with 7.5% acetone/hexane resulting in a N and C-protected 10–11 dipeptide.

A solution of the N and C-protected 10–11 dipeptide (4.65 g, 10.4 mmol) in 40 mL of 2-propanol was flushed with $N_2$ and treated with 500 mg of 10% Pd on carbon. The mixture was placed under hydrogen atmosphere, stirred for 14 hr, then flushed with nitrogen, filtered through a pad of Celite, and concentrated in vacuo. The residue was then treated with 150 mL of 0.5N HCl, which was then washed with ether (2×) made basic with 5% ammonium hydroxide to pH=9, and again washed with ether (3×). These latter extracts were combined, washed with 50% brine and brine, and dried over $MgSO_4$. The compound was then concentrated in vacuo resulting in a C-protected 10–11 dipeptide.

A solution of the C-protected dipeptide (2.75 g, 8.75 mmol) and DIEA (3.2 mL, 18.4 mmol) in 120 mL of $CH_2Cl_2$ was cooled with stirring under inert atmosphere in an ice/water bath. The cold mixture was treated simultaneously with 2.57 g (9.2 mmol) of N-protected nine position amino acid and 2.34 g (9.2 mmol) of BOP-Cl. The mixture was stirred for 24 hr, slowly warming to 10° C. After washing with $H_2O$, 10% $KHSO_4$, 1N $NaHCO_3$, 50% brine, and brine it was dried over $MgSO_4$ and concentrated in vacuo to a yellow oil. Purification on a column of 250 g silica gel, eluting with 7.5% acetone/hexanes yielded a C and N-protected 9–10–11 tripeptide.

Hydrogenation of the C and N-protected 9–10–11 tripeptide was carried out as above for the C and N-protected 10–11 dipeptide using 30 mL of 2-propanol and 300 mg of 10% Pd on Carbon. However in this case treatment of the residue from the hydrogenation mixture with aqueous HCl resulted in the formation of the hydrochloride salt which was treated with 5% $NH_4OH$ and the mixture was extracted with ether (3×). The organic layers were combined, washed with $H_2O$ and brine, dried over $MgSO_4$ and concentrated to yield the C-protected 9–10–11 tripeptide.

A solution of the C-protected 9–10–11 tripeptide (2.33 g, 5.44 mmol) and 1.99 mL (11.1 mmol) DIEA in 75 mL $CH_2Cl_2$ was cooled with stirring under inert atmosphere in an ice/water bath. The cold mixture was treated simultaneously, in one portion with the N-protected eight position amino acid (1.78 g, 5.72 mmol) and BOP-Cl (1.46 g, 5.74 mmol). The mixture was transferred to a 4°–6° C. cold room and allowed to react for 17 hrs. The workup of the product was performed as discussed above for the C and N-protected 9–10–11 tripeptide, and chromatography on 200 g of silica gel, eluting with 15% acetone/hexanes yielded the N and C-protected 8–9–10–11 tetrapeptide fragment (SEQ ID NO:2).

General Procedure C: Synthesis of CsA Hexapeptide Fragment 2–7 (SEQ ID NO:26)

A solution of the six position amino acid N-protected by a Boc group (10.31 g, 42.02 mmol) and DIEA (7.67 mL, 44.0 mmol) in 250 mL of $CH_2Cl_2$ was cooled in an ice/water bath under $N_2$ and treated with 11.21 g (44.02 mmol) of BOP-Cl, and the suspension was stirred vigorously for 2.5 hours. To this mixture was added, in one portion, a solution of the seven position amino acid C-protected by a OBzl group (7.298 g, 40.72 mmol) and DIEA (7.67 mL, 44.0 mmol) in 6 mL of $CH_2Cl_2$. The mixture was placed under a $CaSO_4$ drying tube and stirred overnight in a 5° C. cold room. The solution was then poured into ether (3× volume) and water (2× volume). The organic layer was separated, washed with 10% aqueous $KHSO_4$, $H_2O$, 1N $NaHCO_3$, 50% brine, and brine. After drying over $MgSO_4$ it was concentrated in vacuo and purified by chromatography on 400 g of silica gel, eluting with 10% acetone/hexanes to yield an N and C-protected 6–7 dipeptide.

8.946 g (22 mmol) of the N and C-protected 6–7 dipeptide was deprotected with 50% TFA in methylene chloride to yield, after neutralization, extraction into methylene chloride, and evaporation, a quantitative yield of the C-protected 6–7 dipeptide.

1.9 g (6.2 mmol) of the C-protected 6–7 dipeptide and 2.21 g (8.68 mmol) of BOP-Cl were added to 30 mL of methylene chloride. The suspension was cooled to 0° C. under inert atmosphere and a mixture of N-protected five position amino acid (2.44 g, 8.68 mmol) and DIEA (3.0 mL, 17 mmol) in 30 mL of methylene chloride was added dropwise over 6 hr, to the rapidly stirred suspension. The reaction was stirred for an additional 14 hr at 5° C. and then concentrated to a thick oily residue, which was applied directly to 180 g of silica gel, and eluted with 20–30% EtOAc/hexanes to give an N and C-protected 5–6–7 tripeptide.

5.7 g (10 mmol) of the N and C-protected 5–6–7 tripeptide was added to 1.52 mL (14 mmol) anisole and 7.8 mL of dioxane and cooled to 0° C. under inert atmosphere and treated with a precooled 0° C. solution of 5.8M HCl-dioxane (17.2 mL, 100 mmol of HCl). After being stirred for 2 hr at 0° C. and an additional 12 hr at 5° C. the mixture was rotovaped under reduced pressure. After additional vacuum drying the C-protected 5–6–7 tripeptide was isolated and used directly for the next step.

The four position amino acid, N-protected by an Fmoc group, (4.41 g, 12 mmol) in 120 mL of methylene chloride was chilled to 0° C. under inert atmosphere. To this solution was added oxalyl chloride (2.3 mL, 26.4 mmol) in one portion followed, after several minutes by a catalytic amount of DMF (120 µl). After 2 hr the mixture was concentrated on a rotary evaporator as described in the previous paragraph and was used in the next coupling procedure.

A solution of the C-protected 5–6–7 tripeptide (10.0 mmol) in 30 mL of methylene chloride was cooled to 0° C. under inert atmosphere and treated with the entire yield of the Fmoc-four position amino acid (12.0 mmol) as a solution in 30 mL of methylene chloride. The stirred solution was treated dropwise over 1 hr with DIEA (4.2 mL, 24 mmol) in 30 mL of methylene chloride. After three hours at 0° C. the reaction was diluted with 90 mL methylene chloride and washed with 1M KHSO$_4$ and 50% brine. The organic layer was concentrated, diluted with diethyl ether/ethyl acetate mixture, and washed with saturated NaHCO$_3$, 50% brine, brine. After drying over MgSO$_4$ and concentrating in vacuo, the resulting C and N-protected 4–5–6–7 tetrapeptide (SEQ ID NO:23) was chromatographed on 700 g silica gel.

A solution of the C and N-protected 4–5–6–7 tetrapeptide (SEQ ID NO:23) (3.2 g 6 mmol) in 30 ml CH$_3$CN was treated with an equal volume of DIEA while cooling on ice under inert atmosphere. After being stirred for 3 hr at 0° C., the solution was concentrated in vacuo, and the residue was treated with 20 mL of CH$_3$CN and again concentrated. This was treated with 60 mL of methylene chloride and 2.31 mL (13.2 mmol) of DIEA and then chilled to 0° C. under inert atmosphere. The 2–3 dipeptide was added (1.81 g, 6.6 mmol) along with BOP-Cl (1.83 g, 7.2 mmol) to the ice cold stirred solution. After 5 hr at 0° C. the reaction mixture was concentrated in vacuo and the residue was dissolved in diethyl ether/ethyl acetate mixture. The organic layer was separated, washed with 10% aqueous KHSO$_4$, H$_2$O, 1N NaHCO$_3$, 50% brine, and brine. After drying over MgSO$_4$ it was concentrated in vacuo and purified by chromatography on 400 g of silica gel, eluting with 30% acetone/hexanes to yield and N and C-protected 2–3–4–5–6–7 hexapeptide.

The N and C-protected 2–3–4–5–6–7 hexapeptide (SEQ ID NO:26) was N-deprotected by reaction of 868 mg (1.1 mmol) of the hexapeptide with 5.5 mL of TFA in 1.5 mL of methylene chloride for 14 hr at −15° C. to yield after workup, a C-protected 2–3–4–5–6–7 hexapeptide (SEQ ID NO:26).

General Procedure D: Synthesis of CsA Heptapeptide Fragment 1–7

A suspension of MeBmt or MeLeu(3-OH)(0.2 mmol, 1 equiv) in freshly distilled acetone (60 ml) was heated to reflux under N$_2$ for 24 h until an almost clear solution appeared. The acetonide of MeBmt or MeLeu(3-OH) solution was concentrated in vacuo to 1.5 ml which was directly used for the next coupling reaction without further purification.

A solution of freshly prepared acetonide-protected amino acid (0.2 mmol, 1 equiv) in acetone (1.5 ml) was added 3 ml of THF, N-methylmorpholine (0.22 mmol, 1.1 equiv), 1-hydroxybenzotriazole (0.44 mmol, 2.2 equiv), and hexapeptide amine (0.22 mmol, 1.1 equiv). The resultant mixture was cooled to 0° C. and DCC (0.22 mmol, 1.1 equiv) was added. The mixture was allowed to warm up to room temperature and stirred under N$_2$ for 20 h, after which time the precipitated dicyclohexylurea (DCU) was removed by filtration and washed with small portion of CH$_2$C$_2$. The combined filtrate was washed with saturated NaHCO$_3$ solution and dried over MgSO$_4$. Concentration in vacuo and dissolving the residue in EtOAc yielded more DCU. The residue remaining after a second filtration and concentration in vacuo was purified by chromatography with 10–40% acetone in freshly distilled n-hexane to give the N,O-Isopropylidene protected heptapeptide 1–7.

A solution of N,O-isopropylidene heptapeptide (0.156 mmol) in 3 ml of MeOH was stirred with 1N HCl aqueous solution (0.6 mmol, 4 equiv) at room temperature for 15 hours. The reaction mixture was treated with NaHCO$_3$ (2 mmol) and concentrated in vacuo to a white solid. The residue was taken up in 2% MeOH in CH$_2$Cl$_2$ and flash-chromatographed with 2–4% MeOH in CH$_2$Cl$_2$ to give the 1–7 heptapeptide (SEQ ID NO:18).

General Procedure E: Synthesis of Linear Uncyclized CsA Analog

A solution of N-protected heptapeptide (residue 1–7) (SEQ ID NO:10) (0.1 mmol) and tetrapeptide amine (residue 8–11) (SEQ ID NO:2) (0.15 mmol, 1.5 equiv) in CH$_2$Cl$_2$ (2 ml) was treated sequentially with N-methylmorpholine (0.2 mmol) and BOP-Cl reagent. The reaction mixture was sealed tightly and stirred at room temperature under N$_2$ for 3 days. The mixture was then diluted with CH$_2$Cl$_2$ (15 ml) and water (10 ml). The aqueous layer was extracted with additional CH$_2$Cl$_2$ (3×10 ml) and the combined organic layers were dried over MgSO$_4$ and concentrated in vacuo. The resultant residue was purified by flash chromatography on silica gel with 10–40% acetone in freshly distilled n-hexane to give a pure, fully-protected undecapeptide (SEQ ID NO:27). Some impurities with higher $R_f$, possibly another undecapeptide epimer or unreacted substrates were usually isolated during the chromatographic process.

General Procedure F: Synthesis of Cyclized CsA Analog

A solution of the protected undecapeptide (0.05 mmol) in EtOH (2 ml) was flushed with N$_2$ and cooled to 0° C. The mixture was treated with 0.2N NaOH solution (0.5 ml) and stirred for 1.5 h; an additional portion of 0.2N NaOH solution (0.25 ml) was added and stirring was continued at 0° C. for 3.5–12 hours. The reaction mixture was then neutralized to pH 6 with 0.2N HCl solution (0.75 ml) and washed with brine (10 ml) and CH$_2$Cl$_2$ (20 ml). The aqueous layer was then extracted with additional CH$_2$Cl$_2$ (4×10 ml). The combined organic layers were dried over MgSO$_4$ and concentrated in vacuo to dryness to give a clear oil which was used directly for further reaction.

The oily residue (0.05 mmol) was dissolved in CH$_2$Cl$_2$ (200 ml) and treated sequentially with DMAP (0.25 mmol) and propyl phosphonic anhydride (a 50% w/v solution in CH$_2$Cl$_2$ from Fluka). The reaction mixture was stirred at room temperature under N$_2$ for 2 days, concentrated to 1–2 ml and applied directly to a silica gel column. Flash chromatography with 10–40% acetone in freshly distilled n-hexane gave a pure cyclic undecapeptide compound.

Example 3

Specific Experimental Synthetic Procedure for Preferred CsA Analog, [Me(3-OH)Leu[1],MeAla[4], MeAla[6]]CsA Specific Experimental Procedure A: Synthesis of β-Hydroxy-N methylleucine (MeLeu(3-OH))

Isobutyraldehyde (0.3 ml, 3.2 mmol) and isothiocyanate chiral auxiliary (1.3 g, 4.8 mmol) were condensed to give 0.6 g (54%) of (4S)-3-((4'S,5'R)-5'-isopropyl-2'-thioxo-4'-oxazolidinylcarbonyl)-4-(phenylmethyl)-2-oxazolidinone as a foamy solid.

The aldol adduct (550 mg, 1.58 mmol) was hydrolyzed to afford Methyl (4S,5R)-5-isopropyl-2-thioxo-oxazolidine-4-carboxylate (240 mg (75%)) as a clear oil.

The carboxylate (700 mg, 3.45 mmol) was treated with Meerwein reagent (trimethoxonium tetrafluoroborate) to give 246 mg (35%) of Methyl (4S,5R)-5-isopropyl-3-methyl-2-oxazolidinone-4-carboxylate as a clear oil. The (4R)-Epimer was obtained as a foamy solid (104 mg, 14%).

The methyl ester (150 mg, 0.75 mmol) was hydrolyzed with 0.2N KOH to give, after purification with Sephadex LH-20, 90 mg (75%) of 2S,3R)-3-Hydroxy-N-methylleucine as a white solid.

Specific Experimental Procedure B: Synthesis of CsA Tetrapeptide Fragment 8–11, (D)-Ala-MeLeu-MeLeu-MeVal (SEQ ID NO:2)

[[(9-Fluorenylmethyl)oxy]carbonyl]-D-Alanyl-N-Methyl-L-leucyl-N-Methyl-L-leucyl-N-Methyl-L-Valine t-Butoxy Ester (Fmoc-D-Ala-MeLeu-MeLeu-MeVal-Boc) was synthesized according to the general procedure B in 85% yield and obtained as a foamy solid.

Specific Experimental Procedure C: Synthesis of CsA Hexapeptide Fragment 2–7, Abu-Sar-MeAla-Val-MeAla-Ala (SEQ ID NO:26)

L-2-Aminobutyryl-Sarcosyl-N-Methyl-L-alanyl-L-Valyl-N-Methyl-L-alanyl-L-Alanine Benzyl Ester HLeu-Abu-Sar-MeAla-Val-MeAla-Ala-OBzl) was synthesized according to the general procedure C in 65% yield and obtained as a foamy solid.

Specific Experimental Procedure D: Synthesis of CsA Heptapeptide Fragment 1–7, MeLeu(3-OH)-Abu-Sar-MeAla-Val-MeAla-Ala (SEQ ID NO:5)

(4S,5R)-2,2,3-Trimethyl-5-isopropyl-4-(oxazolidinyl)-carbonyl]-L-2-Aminobutyryl-Sarcosyl-N-Methyl-L-alanyl-L-Valyl-N-Methyl-L-alanyl-L-Alanine Benzyl Ester (N,O-Isopropylidene-Me(3-OH)Leu-Abu-Sar-MeAla-Val-MeAla-Ala-OBzl) was synthesized according to the general procedure D in 55% yield and obtained as a foamy solid.

(2S,3R)-3-Hydroxy-N-methyl-leucyl-L-2-Aminobutyryl-Sarcosyl-N-Methyl-L-alanyl-L-Valyl-N-Methyl-L-alanyl-L-Alanine Benzyl Ester (H-Me(3-OH)Leu-Abu-Sar-MeAla-Val-MeAla-Ala-OBzl) was synthesized according to the general procedure D in 62% yield and obtained as a foamy glass.

Specific Experimental Procedure E: Synthesis of Linear Uncyclized CsA Analog (SEQ ID NO:6)

[[(9-Fluorenylmethyl)oxy]carbonyl]-D-Alanyl-N-Methyl-L-leucyl-N-Methyl-L-leucyl-N-Methyl-L-Valyl-[(2S,3R)-3-hydroxy-N-methyl-leucyl]-L-2-Aminobutyryl-Sarcosyl-N-Methyl-L-alanyl-L-Valyl-N-Methyl-L-alanyl-L-Alanine Benzyl Ester (Fmoc-D-Ala-MeLeu-MeLeu-MeVal-Me(3 -OH)Leu-Abu-Sar-MeAla-Val-MeAla-Ala-OBzl) was synthesized according to the general procedure E in 34% yield and obtained as a foamy solid.

Example 5

Immunostimulatory Properties of CsA Analogs

The novel immunostimulatory properties of the present claimed CsA analogs were determined by the following procedure:

First, PBMC's from a healthy donor were isolated by density centrifugation over histopaque (Sigma). The PBMC's were activated with PHA at 1 µg/ml and plated at 1×10$^5$ cells/well in the presence of both serially diluted CsA or CsA analog. The cells were incubated for 3 days before being pulsed with $^3$H-thymidine and harvested the next day. The amount of radioactivity was determined by scintillation counting. The results are shown in Table 5.

The study was then expanded to examine the immunostimulatory properties of the present claimed CsA analogs by performing the aforementioned procedure on PBMC's obtained from eight additional human donors. The results illustrate a small degree of immunostimulatory variability between individuals, but the tangible nature of the immunostimulatory effect remains constant. This data is shown in Table 6.

Example 6

Solid Phase Synthesis of CsA Analogs

The structure-activity relationships for other biological activities of CsA outside of immunosuppression are totally unknown. The current literature shows that only a small fraction of the possible CsA derivatives have been synthesized to date. In addition, since some CsA substitutions act synergistically, one cannot predict the activities of multiply substituted CsA derivatives from the existing database which is made up mostly from single amino-acid substitutions. The only logical procedure for deducing the structure-function relationship for CsA derivatives is to synthesize large numbers of derivatives and subsequently screen them for biological activity. This procedure requires a new method of synthesizing CsA derivatives, in particular by solid-phase techniques.

During the course of synthesizing the novel CsA analogs, we discovered methods of synthesizing precursors of the CsA analogs by solid phase methods. Although efficient methods for the total synthesis of CsA and analogs in solution have been available for several years, the synthesis of CsA by solid phase synthetic methods has not yet been achieved, in part because conventional coupling procedures with sterically hindered or N-methyl amino acids often result in incomplete couplings under solid phase synthesis conditions, leading to deletion sequences.

Figure 14:
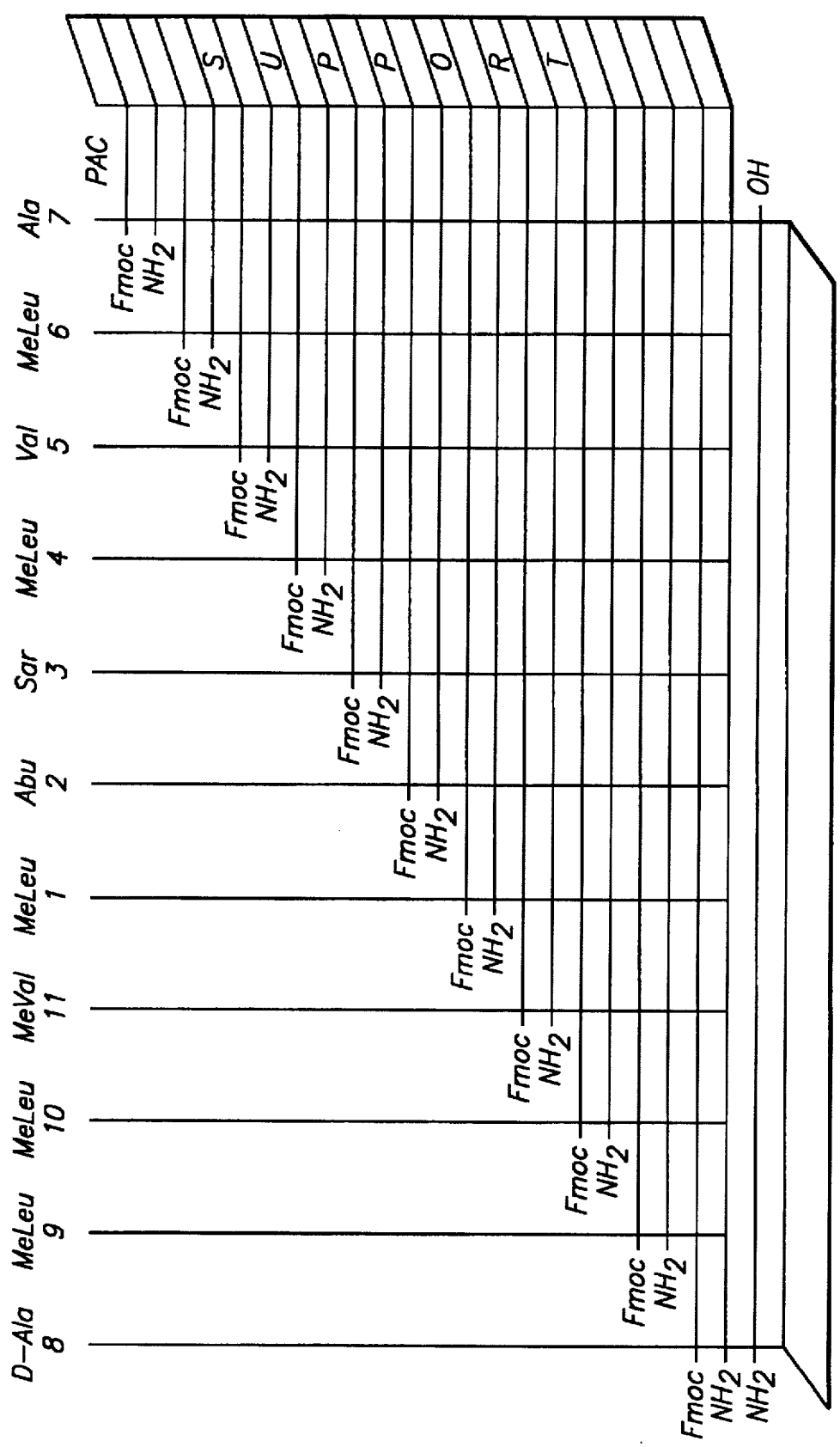
FIG. 14 shows the solid phase synthesis of [MeLeu$^1$]CsA

We were able to subsequently synthesize an entire cyclic CsA derivative using the following solid-phase synthetic procedure, which is outlined in FIG. 14: (SEQ ID NOS:12–26)

1) The cyclosporin analog was synthesized utilizing a PAC (p-alkoxybenzyl alcohol) group to link the growing peptide chain to the MBHA (methylbenzhydrylamine)polystyrene resin.

2) DMF (N,N-dimethylformamide) was used to swell and wash the resin.

3) The first amino acid linked to the support was an Fmoc-amino-protected amino acid in three fold excess which was linked to the resin by reaction with DIPCDI (diisopropylcarbodiimide) in three-fold excess over 90 minutes.

4) The Fmoc group was removed from the first amino acid by reaction with piperidine/DMF (v:v 3:7).

5) The second amino acid linked to the peptide was an Fmoc-amino-protected amino acid in three fold excess which was linked to the resin by reaction with BOP/DIEA in three fold excess over 3 hours.

6) The Fmoc group was removed from the terminal amino acid by reaction with piperidine/DMF (v:v 3:7) in three fold excess.

7) The third amino acid linked to the peptide was an Fmoc-amino-protected amino acid in three-fold excess which was linked to the resin by reaction with HATU

[O-(7-azabenzotriazol-1-yl)-1,1,2,2,-tetramethyluronium hexafluorophosphate]/DIEA in three-fold excess using a double-coupling protocol of 2 (3 hr) couplings.

8) The Fmoc group was removed from the terminal amino acid by reaction with piperidine/DMF (v:v 3:7).

9) Steps 7 and 8 were sequentially repeated until the peptide was eleven amino acids long.

10) The deprotected undecapeptide was cleaved from the resin using TFA:H$_2$O (v:v 95:5) for 4 hours, washed with ether, dried, and purified by reverse-phase high performance liquid chromatography.

11) The undecapeptide was cyclized by reaction with (PrPO$_2$)$_3$ and DMAP in CH$_2$Cl$_2$ solution under highly dilute conditions.

12) The cyclized peptide was obtained in 10–15% yield and purified by column chromatography and characterized by NMR and FABMS.

Figure 15:
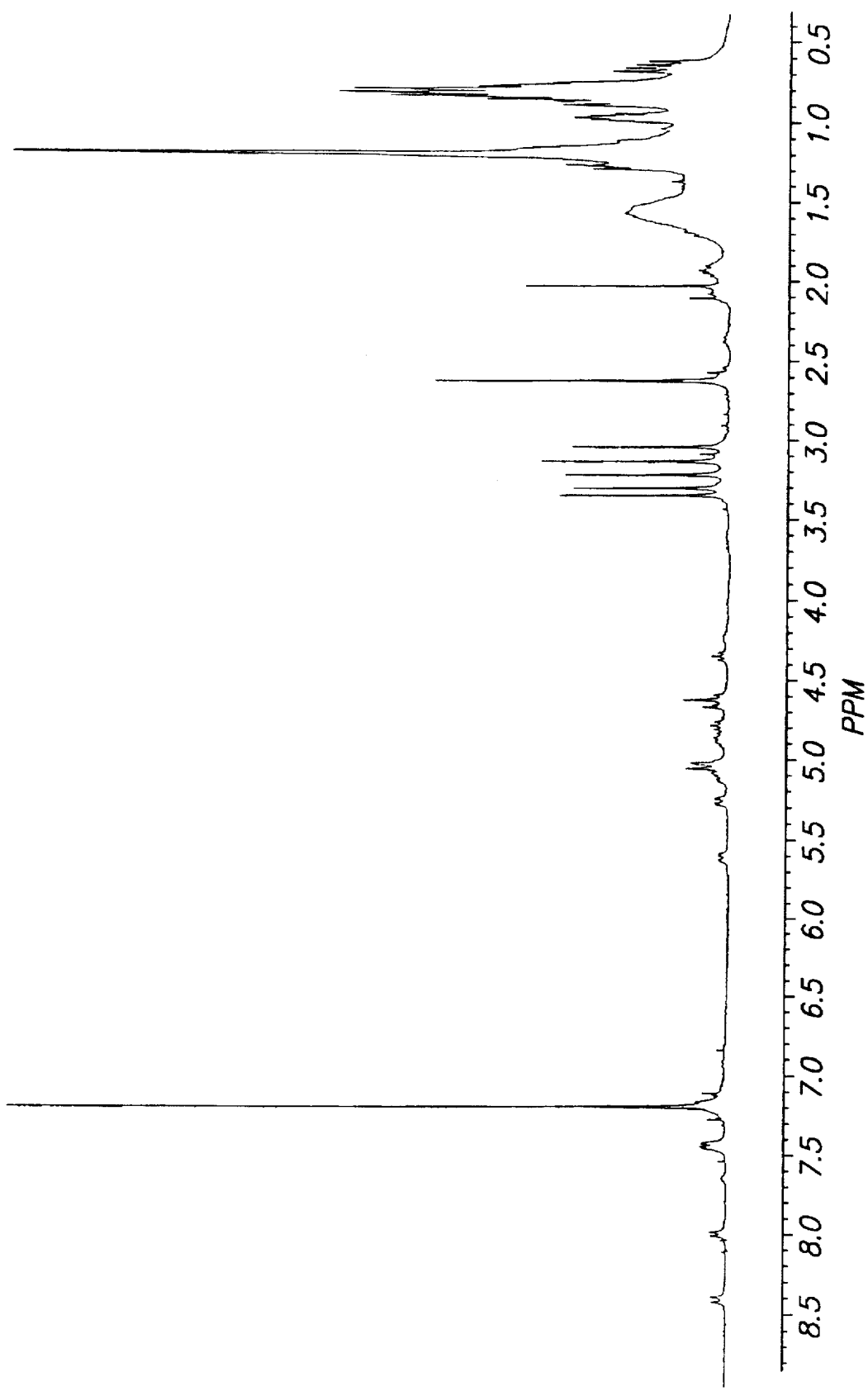
FIG. 15 shows the NMR spectrum of [MeLeu$^1$]CsA synthesized by solid phase methods.
Figure 16:
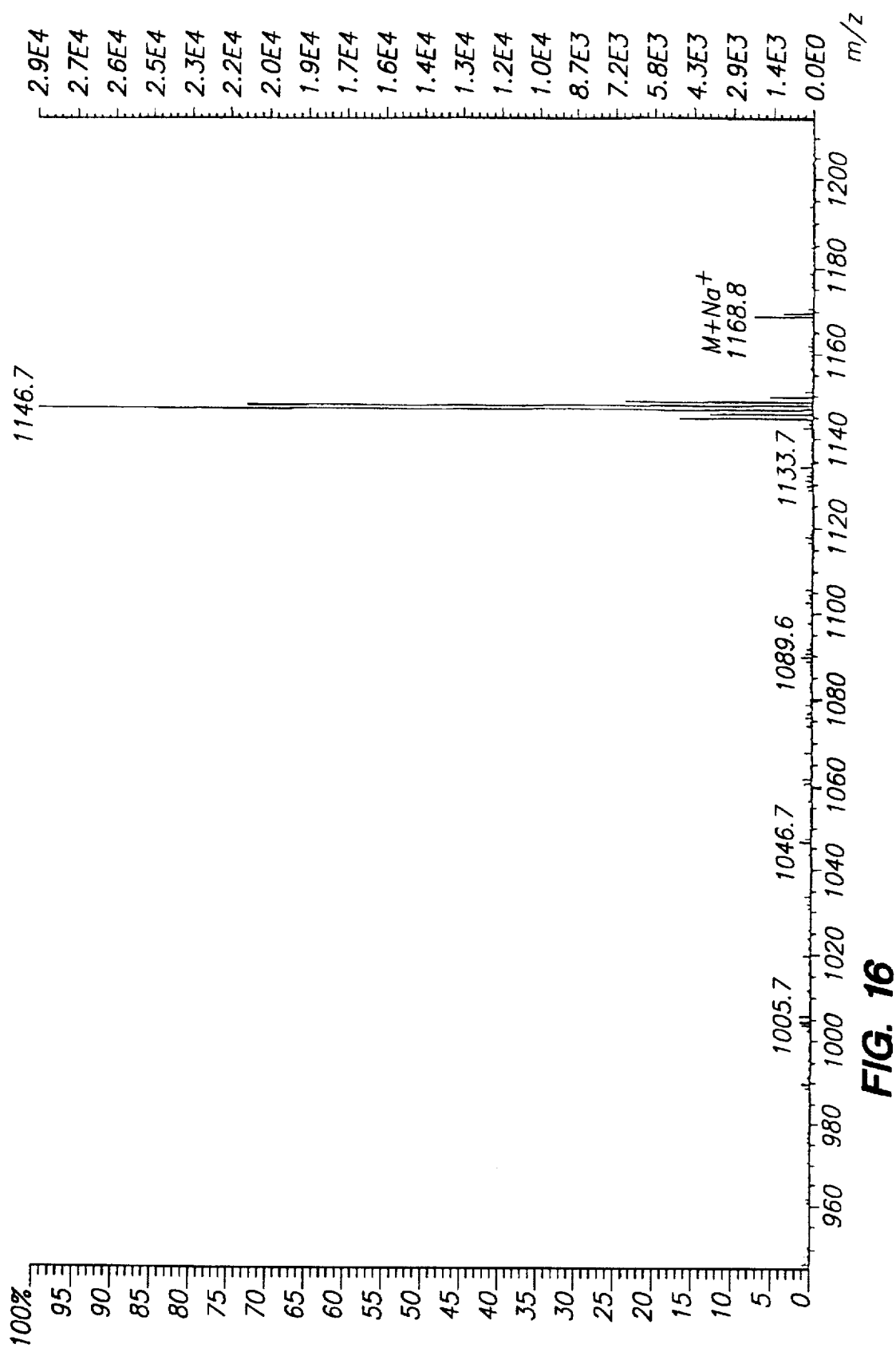
FIG. 16 shows the FABMS spectrum of [MeLeu(3-OH)$^1$]CsA synthesized by solid phase methods.
Figure 17:
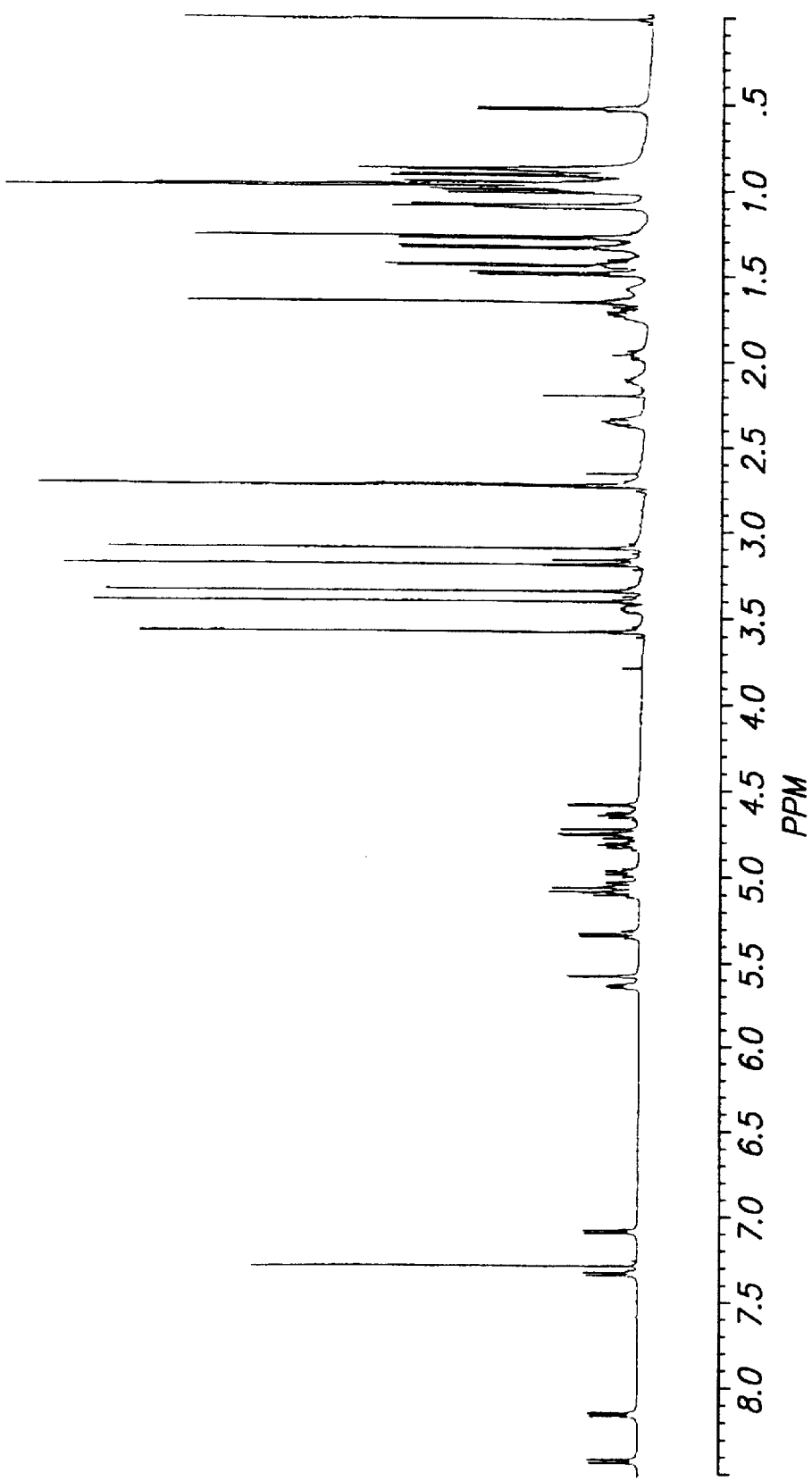
FIG. 17 shows the NMR spectrum of the preferred CsA analog, [MeLeu(3-OH)$^1$,MeAla$^{4,6}$]CsA

Using this procedure the CsA analog [MeLeu$^1$]-CsA was synthesized. The NMR and FABMS spectra are attached at FIGS. 15 and 16 respectively. Using the solid-phase techniques discussed here it is possible to create libraries of CsA analogs using combinatorial methods discussed in the literature. (See a) Gallop, M. A.; Barrett, R. W.; Dower, W. J.; Fodor, S. P. A. and Gordon, E. M.; J. Med. Chem. 37:1233 and b) Gordon, E. M.; Barrett, R. W.; Dower, W. J.; Fodor, S. P. A.; and Gallop, M. A.; J. Med. Chem. 37:1385)

Example 7

Screening CsA Derivatives For Biological Activity

As noted before the preferred CsA derivative is both non-immunosuppressive as well as anti-HIV. The following section outlines a procedure whereby a novel CsA derivative can be screened for potentially useful biological activity.

The Screening Modes consist of the following biological assays:

Mode I: Determine whether the CsA analog of interest inhibits calcineurin and is therefore immunosuppressive.

Mode II: Determine whether the non-immunosuppressive CsA analog of interest inhibits cyclophilin as well as cyclophilin-mediated HIV replication.

Mode III: Determine whether the CsA analog of interest inhibits Heat Shock Protein (hsp70) and evaluate such inhibitors for effects on viral assembly.

Mode IV: Determine whether the CsA analog of interest inhibits HIV protease as well as other proteases.

A new CsA analog ("X") can be evaluated for biological activity using the procedure outlined in Table 7.

Several binding assays are required for assessing the potential of cyclosporin analogs for cyclophilin binding, potential immunosuppression, possible HIV-protease inhibition of hsp70 binding. Sensitive and robust assays are necessary to process the large numbers of CsA analogs created by the solid-phase synthesis described in Example 5. The binding assays described below are used for the screening of the CsA analog libraries. The assays are adapted from the technology developed for ELISA systems and histochemistry over the past twenty years. Such systems are inherently heterogeneous and therefore ideally suited for screening analogs bound to beads. The best candidates from the initial screening are further tested by using more specific assays to probe biological effects. For example, those compounds found not to be immunosuppressive in Mode I can be tested as potential immunostimulatory analogs of CsA in mitogen assays as described in Example 5 above. The screening of the analogs can be accomplished either with the analog attached to the bead on which it was synthesized or in solution, depending on the requirements of the assay.

Sources of Proteins Used in Assays

Cyclophilin (CyP) has been expressed and purified by the inventor to a level of 80 mg purified cyclophilin per liter of culture. HIV protease was obtained in an available recombinant form. Hsp70 was obtained in a pET expression system (the pET expression system is commercially available from Novagen, Madison, Wis.) and was purified. Both the available bovine calcineurin and the human calcineurin subunit A may be used in these studies.

Cyclophilin-Cyclosporin Binary Complex Assays

One method of determining the level of binding between the CsA analog and cyclophilin involves coupling of fluoroscein isothiocyanate to purified cyclophilin using standard conditions. The fluorescent cyelophilin is bound to the cyclosporin linked to the solid phase synthesis beads enabling excess cyclophilin to be removed by a series of washes and the fluorescence detected with a fluorescent plate reader or microscope. The second assay is based on the ELISA method. The assay begins with biotinylating cyclophilin to form the [Biot-CyP] derivative. The binding of resin-CsA to [Biot-CyP] is detected by using alkaline phosphatase and peroxidase coupled to streptavidin which allows the cyclophilin-CsA complex to be measured quantitatively. A variation of this method uses an antibody to cyclophilin to bind the resin-bound cyclosporin analog. The antibody is detected by IgG antibody conjugated with alkaline phosphatase or peroxidase.

The binding of the CsA analogs can be modulated by titrating the complexes with CsA. Increasing CsA concentrations will displace weaker binding CsA analogs. Soluble CsA analogs that bind less tightly to CyP are used to compete off the less active resin-bound CsA derivatives. By controlling the concentration and potency of CsA competitors, it is possible to determine the best inhibitors in each synthetic preparation.

Cyclophilin-Cyclosporin-Calcineurin Ternary Complex Assays

One method of determining the degree of formation of cyclophilin-CsA-calcineurin binding uses the fact that calcineurin binds only to the eyclophilin-CsA complex. Thus addition of calcineurin and cyclophilin to the combinatorial library forms a ternary complex only with CsA analogs that bind to both proteins, a property usually associated with immunosuppressive CsA analogs. Ternary complexes are separated from the excess reagents and quantitated by either fluoroscein labelled calcineurin or by an antibody to calcineurin.

The second assay is based on Amersham's new Scintillation Proximity Assay system (Amersham, Ill.). In this assay, scintillant is covalently linked to a solid phase bead. The radioisotope must be adjacent to the bead in order for light production to take place. Using the biotinylated cyclophilin and streptavidin-SPA beads, the addition of the CsA analog in solution along with I$^{125}$-calcineurin causes scintillation. This method has been shown to be as sensitive as radioimmunoassays. This method can be limited to soluble CsA analogs due to the steric interactions of binding to solid phase beads, but does not require the separation of excess reagents.

HIV Protease and Hsp70 CsA Binary Complexes

The systems described earlier are also used to determine the level of binding to HIV-protease and hsp70 of the CsA analog using the appropriate antibodies, fluoroscein-labelled protein, or biotinylated HIV-protease or biotinylated hsp70 as necessary in place of cyclophilin.

From the above it should be apparent that the present invention provides immunostimulatory analogs of cyclosporin that may be useful in the study of immune cells. Specifically, they have been herein demonstrated to act as co-stimulators. It is clear that such analogs provide simpler costimulators that can be synthesized chemically.

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
        ( A ) LENGTH: 11 amino acids
        ( B ) TYPE: amino acid
        ( C ) STRANDEDNESS: unknown
        ( D ) TOPOLOGY: circular ( i i ) MOLECULE TYPE: peptide ( i x ) FEATURE:
        ( A ) NAME/KEY: Modified-site
        ( B ) LOCATION: 1
        ( D ) OTHER INFORMATION: /note= "MeBmt:
            ( 4 R )-N-methyl-4-butenyl-4-methyl-L-threonine."

( i x ) FEATURE:
        ( A ) NAME/KEY: Modified-site
        ( B ) LOCATION: 2
        ( D ) OTHER INFORMATION: /note= "Abu: alpha-aminobutyric
            acid."

( i x ) FEATURE:
        ( A ) NAME/KEY: Modified-site
        ( B ) LOCATION: 3
        ( D ) OTHER INFORMATION: /note= "Sar: sarcosine."

( i x ) FEATURE:
        ( A ) NAME/KEY: Modified-site
        ( B ) LOCATION: 4
        ( D ) OTHER INFORMATION: /note= "MeLeu: N-methylleucine."

( i x ) FEATURE:
        ( A ) NAME/KEY: Modified-site
        ( B ) LOCATION: 6
        ( D ) OTHER INFORMATION: /note= "MeLeu: N-methylleucine."

( i x ) FEATURE:
        ( A ) NAME/KEY: Modified-site
        ( B ) LOCATION: 8
        ( D ) OTHER INFORMATION: /note= "D-Ala: D-alanine."

( i x ) FEATURE:
        ( A ) NAME/KEY: Modified-site
        ( B ) LOCATION: 9..10
        ( D ) OTHER INFORMATION: /note= "MeLeu: N-methylleucine."

( i x ) FEATURE:
        ( A ) NAME/KEY: Modified-site
        ( B ) LOCATION: 11
        ( D ) OTHER INFORMATION: /note= "MeVal: N-methylvaline."

( x i ) SEQUENCE DESCRIPTION: SEQ ID NO:1:

```
Xaa  Xaa  Xaa  Xaa  Val  Xaa  Ala  Xaa  Xaa  Xaa  Xaa
1                      5                      10
```

( 2 ) INFORMATION FOR SEQ ID NO:2:

( i ) SEQUENCE CHARACTERISTICS:
        ( A ) LENGTH: 4 amino acids
        ( B ) TYPE: amino acid
        ( C ) STRANDEDNESS: unknown
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "D-Ala: D-alanine."

( i x ) FEATURE:
  ( A ) NAME/KEY: Modified-site
  ( B ) LOCATION: 2.3
  ( D ) OTHER INFORMATION: /note= "MeLeu: N-methylleucine."

( i x ) FEATURE:
  ( A ) NAME/KEY: Modified-site
  ( B ) LOCATION: 4
  ( D ) OTHER INFORMATION: /note= "MeVal: N-methylvaline."

( x i ) SEQUENCE DESCRIPTION: SEQ ID NO:2:

Xaa Xaa Xaa Xaa
1

( 2 ) INFORMATION FOR SEQ ID NO:3:

( i ) SEQUENCE CHARACTERISTICS:
  ( A ) LENGTH: 4 amino acids
  ( B ) TYPE: amino acid
  ( C ) STRANDEDNESS: unknown
  ( D ) TOPOLOGY: linear ( i i ) MOLECULE TYPE: peptide ( i x ) FEATURE:
  ( A ) NAME/KEY: Modified-site
  ( B ) LOCATION: 1
  ( D ) OTHER INFORMATION: /note= "MeAla: N-methylalanine."

( i x ) FEATURE:
  ( A ) NAME/KEY: Modified-site
  ( B ) LOCATION: 3
  ( D ) OTHER INFORMATION: /note= "MeAla: N-methylalanine."

( x i ) SEQUENCE DESCRIPTION: SEQ ID NO:3:

Xaa Val Xaa Ala
1

( 2 ) INFORMATION FOR SEQ ID NO:4:

( i ) SEQUENCE CHARACTERISTICS:
  ( A ) LENGTH: 6 amino acids
  ( B ) TYPE: amino acid
  ( C ) STRANDEDNESS: unknown
  ( D ) TOPOLOGY: linear ( i i ) MOLECULE TYPE: peptide ( i x ) FEATURE:
  ( A ) NAME/KEY: Modified-site
  ( B ) LOCATION: 1
  ( D ) OTHER INFORMATION: /note= "Abu: alpha-aminobutyric
    acid."

( i x ) FEATURE:
  ( A ) NAME/KEY: Modified-site
  ( B ) LOCATION: 2
  ( D ) OTHER INFORMATION: /note= "Sar: sarcosine."

( i x ) FEATURE:
  ( A ) NAME/KEY: Modified-site
  ( B ) LOCATION: 3
  ( D ) OTHER INFORMATION: /note= "MeAla: N-methylalanine."

( i x ) FEATURE:
  ( A ) NAME/KEY: Modified-site
  ( B ) LOCATION: 5
  ( D ) OTHER INFORMATION: /note= "MeAla: N-methylalanine."

( x i ) SEQUENCE DESCRIPTION: SEQ ID NO:4:

Xaa Xaa Xaa Val Xaa Ala
1     5

( 2 ) INFORMATION FOR SEQ ID NO:5:

( i ) SEQUENCE CHARACTERISTICS:
        ( A ) LENGTH: 7 amino acids
        ( B ) TYPE: amino acid
        ( C ) STRANDEDNESS: unknown
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "MeLeu(3-OH):
            3-hydroxy-N- methylleucine."

( i x ) FEATURE:
        ( A ) NAME/KEY: Modified-site
        ( B ) LOCATION: 2
        ( D ) OTHER INFORMATION: /note= "Abu: alpha-aminobutyric
            acid."

( i x ) FEATURE:
        ( A ) NAME/KEY: Modified-site
        ( B ) LOCATION: 3
        ( D ) OTHER INFORMATION: /note= "Sar: sarcosine."

( i x ) FEATURE:
        ( A ) NAME/KEY: Modified-site
        ( B ) LOCATION: 4
        ( D ) OTHER INFORMATION: /note= "MeAla: N-methylalanine."

( i x ) FEATURE:
        ( A ) NAME/KEY: Modified-site
        ( B ) LOCATION: 6
        ( D ) OTHER INFORMATION: /note= "MeAla: N-methylalanine."

( x i ) SEQUENCE DESCRIPTION: SEQ ID NO:5:

```
Xaa Xaa Xaa Xaa Val Xaa Ala
1               5
```

( 2 ) INFORMATION FOR SEQ ID NO:6:

( i ) SEQUENCE CHARACTERISTICS:
        ( A ) LENGTH: 11 amino acids
        ( B ) TYPE: amino acid
        ( C ) STRANDEDNESS: unknown
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "D-Ala: D-alanine."

( i x ) FEATURE:
        ( A ) NAME/KEY: Modified-site
        ( B ) LOCATION: 2..3
        ( D ) OTHER INFORMATION: /note= "MeLeu: N-methylleucine."

( i x ) FEATURE:
        ( A ) NAME/KEY: Modified-site
        ( B ) LOCATION: 4
        ( D ) OTHER INFORMATION: /note= "MeVal: N-methylvaline."

( i x ) FEATURE:
        ( A ) NAME/KEY: Modified-site
        ( B ) LOCATION: 5
        ( D ) OTHER INFORMATION: /note= "MeLeu(3-OH):
            3-hydroxy-N- methylleucine."

( i x ) FEATURE:
        ( A ) NAME/KEY: Modified-site
        ( B ) LOCATION: 6
        ( D ) OTHER INFORMATION: /note= "Abu: alpha-aminobutyric
            acid."

(ix) FEATURE:
    (A) NAME/KEY: Modified-site
    (B) LOCATION: 7
    (D) OTHER INFORMATION: /note= "Sar: sarcosine."

(ix) FEATURE:
    (A) NAME/KEY: Modified-site
    (B) LOCATION: 8
    (D) OTHER INFORMATION: /note= "MeAla: N-methylalanine."

(ix) FEATURE:
    (A) NAME/KEY: Modified-site
    (B) LOCATION: 10
    (D) OTHER INFORMATION: /note= "MeAla: N-methylalanine."

(xi) SEQUENCE DESCRIPTION: SEQ ID NO:6:

Xaa Xaa Xaa Xaa Xaa Xaa Xaa Xaa Val Xaa Ala
1               5                   10

(2) INFORMATION FOR SEQ ID NO:7:

(i) SEQUENCE CHARACTERISTICS:
        (A) LENGTH: 11 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Modified-site
        (B) LOCATION: 1
        (D) OTHER INFORMATION: /note= "D-Ala: D-alanine."

(ix) FEATURE:
        (A) NAME/KEY: Modified-site
        (B) LOCATION: 2..3
        (D) OTHER INFORMATION: /note= "MeLeu: N-methylleucine."

(ix) FEATURE:
        (A) NAME/KEY: Modified-site
        (B) LOCATION: 4
        (D) OTHER INFORMATION: /note= "MeVal: N-methylvaline."

(ix) FEATURE:
        (A) NAME/KEY: Modified-site
        (B) LOCATION: 5
        (D) OTHER INFORMATION: /note= "MeLeu(3-OH):
            3-hydroxy-N- methylleucine."

(ix) FEATURE:
        (A) NAME/KEY: Modified-site
        (B) LOCATION: 6
        (D) OTHER INFORMATION: /note= "Abu: alpha-aminobutyric
            acid."

(ix) FEATURE:
        (A) NAME/KEY: Modified-site
        (B) LOCATION: 7
        (D) OTHER INFORMATION: /note= "Sar: sarcosine."

(ix) FEATURE:
        (A) NAME/KEY: Modified-site
        (B) LOCATION: 8
        (D) OTHER INFORMATION: /note= "MeAla: N-methylalanine."

(ix) FEATURE:
        (A) NAME/KEY: Modified-site
        (B) LOCATION: 10
        (D) OTHER INFORMATION: /note= "MeAla: N-methylalanine."

(xi) SEQUENCE DESCRIPTION: SEQ ID NO:7:

Xaa Xaa Xaa Xaa Xaa Xaa Xaa Xaa Val Xaa Ala
1               5                   10

(2) INFORMATION FOR SEQ ID NO:8:

( i ) SEQUENCE CHARACTERISTICS:
    ( A ) LENGTH: 7 amino acids
    ( B ) TYPE: amino acid
    ( C ) STRANDEDNESS: unknown
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note= "MeLeu(3-OH):
        3-hydroxy-N- methylleucine."

( i x ) FEATURE:
    ( A ) NAME/KEY: Modified-site
    ( B ) LOCATION: 2
    ( D ) OTHER INFORMATION: /note= "Abu: alpha-aminobutyric
        acid."

( i x ) FEATURE:
    ( A ) NAME/KEY: Modified-site
    ( B ) LOCATION: 3
    ( D ) OTHER INFORMATION: /note= "Sar: sarcosine."

( i x ) FEATURE:
    ( A ) NAME/KEY: Modified-site
    ( B ) LOCATION: 4
    ( D ) OTHER INFORMATION: /note= "MeLeu: N-methylleucine."

( i x ) FEATURE:
    ( A ) NAME/KEY: Modified-site
    ( B ) LOCATION: 6
    ( D ) OTHER INFORMATION: /note= "MeLeu: N-methylleucine."

( x i ) SEQUENCE DESCRIPTION: SEQ ID NO:8:

Xaa Xaa Xaa Xaa Val Xaa Ala
1                 5

( 2 ) INFORMATION FOR SEQ ID NO:9:

( i ) SEQUENCE CHARACTERISTICS:
        ( A ) LENGTH: 11 amino acids
        ( B ) TYPE: amino acid
        ( C ) STRANDEDNESS: unknown
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "D-Ala: D-alanine."

( i x ) FEATURE:
        ( A ) NAME/KEY: Modified-site
        ( B ) LOCATION: 2..3
        ( D ) OTHER INFORMATION: /note= "MeLeu: N-methylleucine."

( i x ) FEATURE:
        ( A ) NAME/KEY: Modified-site
        ( B ) LOCATION: 4
        ( D ) OTHER INFORMATION: /note= "D-MeVal:
            D-N- methylvaline."

( i x ) FEATURE:
        ( A ) NAME/KEY: Modified-site
        ( B ) LOCATION: 5
        ( D ) OTHER INFORMATION: /note= "MeLeu(OH):
            hydroxy-N- methylleucine."

( i x ) FEATURE:
        ( A ) NAME/KEY: Modified-site
        ( B ) LOCATION: 6
        ( D ) OTHER INFORMATION: /note= "Abu: alpha-aminobutyric
            acid."

( i x ) FEATURE:
    ( A ) NAME/KEY: Modified-site
    ( B ) LOCATION: 7
    ( D ) OTHER INFORMATION: /note= "Sar: sarcosine."

( i x ) FEATURE:
    ( A ) NAME/KEY: Modified-site
    ( B ) LOCATION: 8
    ( D ) OTHER INFORMATION: /note= "MeLeu: N-methylleucine."

( i x ) FEATURE:
    ( A ) NAME/KEY: Modified-site
    ( B ) LOCATION: 10
    ( D ) OTHER INFORMATION: /note= "MeLeu: N-methylleucine."

( x i ) SEQUENCE DESCRIPTION: SEQ ID NO:9:

Xaa Xaa Xaa Xaa Xaa Xaa Xaa Xaa Val Xaa Ala
1                5                            10

( 2 ) INFORMATION FOR SEQ ID NO:10:

( i ) SEQUENCE CHARACTERISTICS:
        ( A ) LENGTH: 7 amino acids
        ( B ) TYPE: amino acid
        ( C ) STRANDEDNESS: unknown
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "MeBmt:
            ( 4 R )-N-methyl-4-butenyl-4-methyl-L-threonine."

( i x ) FEATURE:
        ( A ) NAME/KEY: Modified-site
        ( B ) LOCATION: 2
        ( D ) OTHER INFORMATION: /note= "Abu: alpha-aminobutyric
            acid."

( i x ) FEATURE:
        ( A ) NAME/KEY: Modified-site
        ( B ) LOCATION: 3
        ( D ) OTHER INFORMATION: /note= "Sar: sarcosine."

( i x ) FEATURE:
        ( A ) NAME/KEY: Modified-site
        ( B ) LOCATION: 4
        ( D ) OTHER INFORMATION: /note= "MeLeu: N-methylleucine."

( i x ) FEATURE:
        ( A ) NAME/KEY: Modified-site
        ( B ) LOCATION: 6
        ( D ) OTHER INFORMATION: /note= "MeLeu: N-methylleucine."

( x i ) SEQUENCE DESCRIPTION: SEQ ID NO:10:

Xaa Xaa Xaa Xaa Val Xaa Ala
1                5

( 2 ) INFORMATION FOR SEQ ID NO:11:

( i ) SEQUENCE CHARACTERISTICS:
        ( A ) LENGTH: 11 amino acids
        ( B ) TYPE: amino acid
        ( C ) STRANDEDNESS: unknown
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "D-Ala: D-alanine."

( i x ) FEATURE:

( A ) NAME/KEY: Modified-site
( B ) LOCATION: 2.3
( D ) OTHER INFORMATION: /note= "MeLeu: N-methylleucine."

( i x ) FEATURE:
( A ) NAME/KEY: Modified-site
( B ) LOCATION: 4
( D ) OTHER INFORMATION: /note= "D-MeVal:
D-N- methylvaline."

( i x ) FEATURE:
( A ) NAME/KEY: Modified-site
( B ) LOCATION: 5
( D ) OTHER INFORMATION: /note= "McBmt:
( 4 R )-N-methyl-4-butenyl-4-methyl-L-threonine."

( i x ) FEATURE:
( A ) NAME/KEY: Modified-site
( B ) LOCATION: 6
( D ) OTHER INFORMATION: /note= "Abu: alpha-aminobutyric
acid."

( i x ) FEATURE:
( A ) NAME/KEY: Modified-site
( B ) LOCATION: 7
( D ) OTHER INFORMATION: /note= "Sar: sarcosine."

( i x ) FEATURE:
( A ) NAME/KEY: Modified-site
( B ) LOCATION: 8
( D ) OTHER INFORMATION: /note= "MeLeu: N-methylleucine."

( i x ) FEATURE:
( A ) NAME/KEY: Modified-site
( B ) LOCATION: 10
( D ) OTHER INFORMATION: /note= "MeLeu: N-methylleucine."

( x i ) SEQUENCE DESCRIPTION: SEQ ID NO:11:

Xaa Xaa Xaa Xaa Xaa Xaa Xaa Xaa Val Xaa Ala
1               5                   10

( 2 ) INFORMATION FOR SEQ ID NO:12:

( i ) SEQUENCE CHARACTERISTICS:
( A ) LENGTH: 11 amino acids
( B ) TYPE: amino acid
( C ) STRANDEDNESS: unknown
( D ) TOPOLOGY: linear ( i i ) MOLECULE TYPE: peptide ( i x ) FEATURE:
( A ) NAME/KEY: Modified-site
( B ) LOCATION: 2
( D ) OTHER INFORMATION: /note= "MeLeu: N-methylleucine."

( i x ) FEATURE:
( A ) NAME/KEY: Modified-site
( B ) LOCATION: 4
( D ) OTHER INFORMATION: /note= "MeLeu: N-methylleucine."

( i x ) FEATURE:
( A ) NAME/KEY: Modified-site
( B ) LOCATION: 5
( D ) OTHER INFORMATION: /note= "Sar: sarcosine."

( i x ) FEATURE:
( A ) NAME/KEY: Modified-site
( B ) LOCATION: 6
( D ) OTHER INFORMATION: /note= "Abu: alpha-aminobutyric
acid."

( i x ) FEATURE:
( A ) NAME/KEY: Modified-site
( B ) LOCATION: 7
( D ) OTHER INFORMATION: /note= "MeLeu: N-methylleucine."

( i x ) FEATURE:

(A) NAME/KEY: Modified-site
(B) LOCATION: 8
(D) OTHER INFORMATION: /note= "MeVal: N-methylvaline."

(ix) FEATURE:
(A) NAME/KEY: Modified-site
(B) LOCATION: 9..10
(D) OTHER INFORMATION: /note= "MeLeu: N-methylleucine."

(ix) FEATURE:
(A) NAME/KEY: Modified-site
(B) LOCATION: 11
(D) OTHER INFORMATION: /note= "D-Ala: D-alanine."

(xi) SEQUENCE DESCRIPTION: SEQ ID NO:12:

Ala Xaa Val Xaa Xaa Xaa Xaa Xaa Xaa Xaa Xaa
1               5                           10

(2) INFORMATION FOR SEQ ID NO:13:

(i) SEQUENCE CHARACTERISTICS:
(A) LENGTH: 4 amino acids
(B) TYPE: amino acid
(C) STRANDEDNESS: unknown
(D) TOPOLOGY: linear (ii) MOLECULE TYPE: peptide (ix) FEATURE:
(A) NAME/KEY: Modified-site
(B) LOCATION: 2
(D) OTHER INFORMATION: /note= "MeLeu: N-methylleucine."

(ix) FEATURE:
(A) NAME/KEY: Modified-site
(B) LOCATION: 4
(D) OTHER INFORMATION: /note= "MeLeu: N-methylleucine."

(xi) SEQUENCE DESCRIPTION: SEQ ID NO:13:

Ala Xaa Val Xaa
1

(2) INFORMATION FOR SEQ ID NO:14:

(i) SEQUENCE CHARACTERISTICS:
(A) LENGTH: 5 amino acids
(B) TYPE: amino acid
(C) STRANDEDNESS: unknown
(D) TOPOLOGY: linear (ii) MOLECULE TYPE: peptide (ix) FEATURE:
(A) NAME/KEY: Modified-site
(B) LOCATION: 2
(D) OTHER INFORMATION: /note= "MeLeu: N-methylleucine."

(ix) FEATURE:
(A) NAME/KEY: Modified-site
(B) LOCATION: 4
(D) OTHER INFORMATION: /note= "MeLeu: N-methylleucine."

(ix) FEATURE:
(A) NAME/KEY: Modified-site
(B) LOCATION: 5
(D) OTHER INFORMATION: /note= "Sar: sarcosine."

(xi) SEQUENCE DESCRIPTION: SEQ ID NO:14:

Ala Xaa Val Xaa Xaa
1               5

(2) INFORMATION FOR SEQ ID NO:15:

(i) SEQUENCE CHARACTERISTICS:

(A) LENGTH: 5 amino acids
(B) TYPE: amino acid
(C) STRANDEDNESS: unknown
(D) TOPOLOGY: linear (ii) MOLECULE TYPE: peptide (ix) FEATURE:
(A) NAME/KEY: Modified-site
(B) LOCATION: 2
(D) OTHER INFORMATION: /note= "MeLeu: N-methylleucine."

(ix) FEATURE:
(A) NAME/KEY: Modified-site
(B) LOCATION: 4
(D) OTHER INFORMATION: /note= "MeLeu: N-methylleucine."

(ix) FEATURE:
(A) NAME/KEY: Modified-site
(B) LOCATION: 5
(D) OTHER INFORMATION: /note= "Abu: alpha-aminobutyric acid."

(xi) SEQUENCE DESCRIPTION: SEQ ID NO:15:

Ala Xaa Val Xaa Xaa
1             5

(2) INFORMATION FOR SEQ ID NO:16:

(i) SEQUENCE CHARACTERISTICS:
(A) LENGTH: 6 amino acids
(B) TYPE: amino acid
(C) STRANDEDNESS: unknown
(D) TOPOLOGY: linear (ii) MOLECULE TYPE: peptide (ix) FEATURE:
(A) NAME/KEY: Modified-site
(B) LOCATION: 2
(D) OTHER INFORMATION: /note= "MeLeu: N-methylleucine."

(ix) FEATURE:
(A) NAME/KEY: Modified-site
(B) LOCATION: 4
(D) OTHER INFORMATION: /note= "MeLeu: N-methylleucine."

(ix) FEATURE:
(A) NAME/KEY: Modified-site
(B) LOCATION: 5
(D) OTHER INFORMATION: /note= "Abu: alpha-aminobutyric acid."

(ix) FEATURE:
(A) NAME/KEY: Modified-site
(B) LOCATION: 6
(D) OTHER INFORMATION: /note= "MeLeu: N-methylleucine."

(xi) SEQUENCE DESCRIPTION: SEQ ID NO:16:

Ala Xaa Val Xaa Xaa Xaa
1             5

(2) INFORMATION FOR SEQ ID NO:17:

(i) SEQUENCE CHARACTERISTICS:
(A) LENGTH: 7 amino acids
(B) TYPE: amino acid
(C) STRANDEDNESS: unknown
(D) TOPOLOGY: linear (ii) MOLECULE TYPE: peptide (ix) FEATURE:
(A) NAME/KEY: Modified-site
(B) LOCATION: 2
(D) OTHER INFORMATION: /note= "MeLeu: N-methylleucine."

( i x ) FEATURE:
    ( A ) NAME/KEY: Modified-site
    ( B ) LOCATION: 4
    ( D ) OTHER INFORMATION: /note= "MeLeu: N-methylleucine."

( i x ) FEATURE:
    ( A ) NAME/KEY: Modified-site
    ( B ) LOCATION: 5
    ( D ) OTHER INFORMATION: /note= "Abu: alpha-aminobutyric acid."

( i x ) FEATURE:
    ( A ) NAME/KEY: Modified-site
    ( B ) LOCATION: 6
    ( D ) OTHER INFORMATION: /note= "MeLeu: N-methylleucine."

( i x ) FEATURE:
    ( A ) NAME/KEY: Modified-site
    ( B ) LOCATION: 7
    ( D ) OTHER INFORMATION: /note= "MeVal: N-methylvaline."

( x i ) SEQUENCE DESCRIPTION: SEQ ID NO:17:

```
Ala  Xaa  Val  Xaa  Xaa  Xaa  Xaa
 1                  5
```

( 2 ) INFORMATION FOR SEQ ID NO:18:

( i ) SEQUENCE CHARACTERISTICS:
    ( A ) LENGTH: 8 amino acids
    ( B ) TYPE: amino acid
    ( C ) STRANDEDNESS: unknown
    ( D ) TOPOLOGY: linear ( i i ) MOLECULE TYPE: peptide ( i x ) FEATURE:
    ( A ) NAME/KEY: Modified-site
    ( B ) LOCATION: 2
    ( D ) OTHER INFORMATION: /note= "MeLeu: N-methylleucine."

( i x ) FEATURE:
    ( A ) NAME/KEY: Modified-site
    ( B ) LOCATION: 4
    ( D ) OTHER INFORMATION: /note= "MeLeu: N-methylleucine."

( i x ) FEATURE:
    ( A ) NAME/KEY: Modified-site
    ( B ) LOCATION: 5
    ( D ) OTHER INFORMATION: /note= "Abu: alpha-aminobutyric acid."

( i x ) FEATURE:
    ( A ) NAME/KEY: Modified-site
    ( B ) LOCATION: 6
    ( D ) OTHER INFORMATION: /note= "MeLeu: N-methylleucine."

( i x ) FEATURE:
    ( A ) NAME/KEY: Modified-site
    ( B ) LOCATION: 7
    ( D ) OTHER INFORMATION: /note= "MeVal: N-methylvaline."

( i x ) FEATURE:
    ( A ) NAME/KEY: Modified-site
    ( B ) LOCATION: 8
    ( D ) OTHER INFORMATION: /note= "MeLeu: N-methylleucine."

( x i ) SEQUENCE DESCRIPTION: SEQ ID NO:18:

```
Ala  Xaa  Val  Xaa  Xaa  Xaa  Xaa  Xaa
 1                  5
```

( 2 ) INFORMATION FOR SEQ ID NO:19:

( i ) SEQUENCE CHARACTERISTICS:
    ( A ) LENGTH: 9 amino acids
    ( B ) TYPE: amino acid (C) STRANDEDNESS: unknown
(D) TOPOLOGY: linear (ii) MOLECULE TYPE: peptide (ix) FEATURE:
 (A) NAME/KEY: Modified-site
 (B) LOCATION: 2
 (D) OTHER INFORMATION: /note= "MeLeu: N-methylleucine."

(ix) FEATURE:
 (A) NAME/KEY: Modified-site
 (B) LOCATION: 4
 (D) OTHER INFORMATION: /note= "MeLeu: N-methylleucine."

(ix) FEATURE:
 (A) NAME/KEY: Modified-site
 (B) LOCATION: 5
 (D) OTHER INFORMATION: /note= "Abu: alpha-aminobutyric acid."

(ix) FEATURE:
 (A) NAME/KEY: Modified-site
 (B) LOCATION: 6
 (D) OTHER INFORMATION: /note= "MeLeu: N-methylleucine."

(ix) FEATURE:
 (A) NAME/KEY: Modified-site
 (B) LOCATION: 7
 (D) OTHER INFORMATION: /note= "MeVal: N-methylvaline."

(ix) FEATURE:
 (A) NAME/KEY: Modified-site
 (B) LOCATION: 8..9
 (D) OTHER INFORMATION: /note= "MeLeu: N-methylleucine."

(xi) SEQUENCE DESCRIPTION: SEQ ID NO:19:

Ala Xaa Val Xaa Xaa Xaa Xaa Xaa Xaa
1               5

(2) INFORMATION FOR SEQ ID NO:20:

(i) SEQUENCE CHARACTERISTICS:
  (A) LENGTH: 10 amino acids
  (B) TYPE: amino acid
  (C) STRANDEDNESS: unknown
  (D) TOPOLOGY: linear (ii) MOLECULE TYPE: peptide (ix) FEATURE:
 (A) NAME/KEY: Modified-site
 (B) LOCATION: 2
 (D) OTHER INFORMATION: /note= "MeLeu: N-methylleucine."

(ix) FEATURE:
 (A) NAME/KEY: Modified-site
 (B) LOCATION: 4
 (D) OTHER INFORMATION: /note= "MeLeu: N-methylleucine."

(ix) FEATURE:
 (A) NAME/KEY: Modified-site
 (B) LOCATION: 5
 (D) OTHER INFORMATION: /note= "Abu: alpha-aminobutyric acid."

(ix) FEATURE:
 (A) NAME/KEY: Modified-site
 (B) LOCATION: 6
 (D) OTHER INFORMATION: /note= "MeLeu: N-methylleucine."

(ix) FEATURE:
 (A) NAME/KEY: Modified-site
 (B) LOCATION: 7
 (D) OTHER INFORMATION: /note= "MeVal: N-methylvaline."

(ix) FEATURE:
 (A) NAME/KEY: Modified-site ( B ) LOCATION: 8..9
( D ) OTHER INFORMATION: /note= "MeLeu: N-methylleucine."

( i x ) FEATURE:
( A ) NAME/KEY: Modified-site
( B ) LOCATION: 10
( D ) OTHER INFORMATION: /note= "D-Ala: D-alanine."

( x i ) SEQUENCE DESCRIPTION: SEQ ID NO:20:

Ala Xaa Val Xaa Xaa Xaa Xaa Xaa Xaa Xaa
1               5                           10

( 2 ) INFORMATION FOR SEQ ID NO:21:

( i ) SEQUENCE CHARACTERISTICS:
( A ) LENGTH: 11 amino acids
( B ) TYPE: amino acid
( C ) STRANDEDNESS: unknown
( D ) TOPOLOGY: circular ( i i ) MOLECULE TYPE: peptide ( i x ) FEATURE:
( A ) NAME/KEY: Modified-site
( B ) LOCATION: 1
( D ) OTHER INFORMATION: /note= "MeLeu(3-OH):
3-hydroxy-N- methylleucine."

( i x ) FEATURE:
( A ) NAME/KEY: Modified-site
( B ) LOCATION: 2
( D ) OTHER INFORMATION: /note= "Abu: alpha-aminobutyric
acid."

( i x ) FEATURE:
( A ) NAME/KEY: Modified-site
( B ) LOCATION: 3
( D ) OTHER INFORMATION: /note= "Sar: sarcosine."

( i x ) FEATURE:
( A ) NAME/KEY: Modified-site
( B ) LOCATION: 4
( D ) OTHER INFORMATION: /note= "MeAla: N-methylalanine."

( i x ) FEATURE:
( A ) NAME/KEY: Modified-site
( B ) LOCATION: 6
( D ) OTHER INFORMATION: /note= "MeAla: N-methylalanine."

( i x ) FEATURE:
( A ) NAME/KEY: Modified-site
( B ) LOCATION: 8
( D ) OTHER INFORMATION: /note= "D-Ala: D-alanine."

( i x ) FEATURE:
( A ) NAME/KEY: Modified-site
( B ) LOCATION: 9..10
( D ) OTHER INFORMATION: /note= "MeLeu: N-methylleucine."

( i x ) FEATURE:
( A ) NAME/KEY: Modified-site
( B ) LOCATION: 11
( D ) OTHER INFORMATION: /note= "MeVal: N-methylvaline."

( x i ) SEQUENCE DESCRIPTION: SEQ ID NO:21:

Xaa Xaa Xaa Xaa Val Xaa Ala Xaa Xaa Xaa Xaa
1               5                           10

( 2 ) INFORMATION FOR SEQ ID NO:22:

( i ) SEQUENCE CHARACTERISTICS:
( A ) LENGTH: 4 amino acids
( B ) TYPE: amino acid
( C ) STRANDEDNESS: unknown
( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note= "MeLeu: N-methylleucine."

( i x ) FEATURE:
    ( A ) NAME/KEY: Modified-site
    ( B ) LOCATION: 3
    ( D ) OTHER INFORMATION: /note= "MeLeu: N-methylleucine."

( x i ) SEQUENCE DESCRIPTION: SEQ ID NO:22:

Xaa Val Xaa Ala
1

( 2 ) INFORMATION FOR SEQ ID NO:23:

( i ) SEQUENCE CHARACTERISTICS:
    ( A ) LENGTH: 4 amino acids
    ( B ) TYPE: amino acid
    ( C ) STRANDEDNESS: unknown
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note= "MeLeu: N-methylleucine."

( i x ) FEATURE:
    ( A ) NAME/KEY: Modified-site
    ( B ) LOCATION: 3
    ( D ) OTHER INFORMATION: /note= "MeAla: N-methylalanine."

( x i ) SEQUENCE DESCRIPTION: SEQ ID NO:23:

Xaa Val Xaa Ala
1

( 2 ) INFORMATION FOR SEQ ID NO:24:

( i ) SEQUENCE CHARACTERISTICS:
    ( A ) LENGTH: 6 amino acids
    ( B ) TYPE: amino acid
    ( C ) STRANDEDNESS: unknown
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note= "Abu: alpha-aminobutyric
        acid."

( i x ) FEATURE:
    ( A ) NAME/KEY: Modified-site
    ( B ) LOCATION: 2
    ( D ) OTHER INFORMATION: /note= "Sar: sarcosine."

( i x ) FEATURE:
    ( A ) NAME/KEY: Modified-site
    ( B ) LOCATION: 3
    ( D ) OTHER INFORMATION: /note= "MeLeu: N-methylleucine."

( i x ) FEATURE:
    ( A ) NAME/KEY: Modified-site
    ( B ) LOCATION: 5
    ( D ) OTHER INFORMATION: /note= "MeLeu: N-methylleucine."

( x i ) SEQUENCE DESCRIPTION: SEQ ID NO:24:

Xaa Xaa Xaa Val Xaa Ala
1              5

( 2 ) INFORMATION FOR SEQ ID NO:25:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Abu: alpha-aminobutyric acid."

( i x ) FEATURE:
        ( A ) NAME/KEY: Modified-site
        ( B ) LOCATION: 2
        ( D ) OTHER INFORMATION: /note= "Sar: sarcosine."

( i x ) FEATURE:
        ( A ) NAME/KEY: Modified-site
        ( B ) LOCATION: 3
        ( D ) OTHER INFORMATION: /note= "MeLeu: N-methylleucine."

( i x ) FEATURE:
        ( A ) NAME/KEY: Modified-site
        ( B ) LOCATION: 5
        ( D ) OTHER INFORMATION: /note= "MeAla: N-methylalanine."

( x i ) SEQUENCE DESCRIPTION: SEQ ID NO:25:

Xaa Xaa Xaa Val Xaa Ala
1                 5

( 2 ) INFORMATION FOR SEQ ID NO:26:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Abu: alpha-aminobutyric acid."

( i x ) FEATURE:
        ( A ) NAME/KEY: Modified-site
        ( B ) LOCATION: 2
        ( D ) OTHER INFORMATION: /note= "Sar: sarcosine."

( i x ) FEATURE:
        ( A ) NAME/KEY: Modified-site
        ( B ) LOCATION: 3
        ( D ) OTHER INFORMATION: /note= "MeAla: N-methylalanine."

( i x ) FEATURE:
        ( A ) NAME/KEY: Modified-site
        ( B ) LOCATION: 5
        ( D ) OTHER INFORMATION: /note= "MeAla: N-methylalanine."

( x i ) SEQUENCE DESCRIPTION: SEQ ID NO:26:

Xaa Xaa Xaa Val Xaa Ala
1                 5

( 2 ) INFORMATION FOR SEQ ID NO:27:

( i ) SEQUENCE CHARACTERISTICS:
        ( A ) LENGTH: 11 amino acids
        ( B ) TYPE: amino acid (C) STRANDEDNESS: unknown
(D) TOPOLOGY: linear (ii) MOLECULE TYPE: peptide (ix) FEATURE:
(A) NAME/KEY: Modified-site
(B) LOCATION: 1
(D) OTHER INFORMATION: /note= "D-Ala: D-alanine."

(ix) FEATURE:
(A) NAME/KEY: Modified-site
(B) LOCATION: 2.3
(D) OTHER INFORMATION: /note= "MeLeu: N-methylleucine."

(ix) FEATURE:
(A) NAME/KEY: Modified-site
(B) LOCATION: 4
(D) OTHER INFORMATION: /note= "D-MeVal:
D-N- methylvaline."

(ix) FEATURE:
(A) NAME/KEY: Modified-site
(B) LOCATION: 5
(D) OTHER INFORMATION: /note= "MeBmt:
(4R)-N-methyl-4-butenyl-4-methyl-L-threonine."

(ix) FEATURE:
(A) NAME/KEY: Modified-site
(B) LOCATION: 6
(D) OTHER INFORMATION: /note= "Abu: alpha-aminobutyric
acid."

(ix) FEATURE:
(A) NAME/KEY: Modified-site
(B) LOCATION: 7
(D) OTHER INFORMATION: /note= "Sar: sarcosine."

(ix) FEATURE:
(A) NAME/KEY: Modified-site
(B) LOCATION: 8
(D) OTHER INFORMATION: /note= "MeLeu: N-methylleucine."

(ix) FEATURE:
(A) NAME/KEY: Modified-site
(B) LOCATION: 10
(D) OTHER INFORMATION: /note= "MeLeu: N-methylleucine."

(xi) SEQUENCE DESCRIPTION: SEQ ID NO:27:

Xaa Xaa Xaa Xaa Xaa Xaa Xaa Xaa Val Xaa Ala
1               5                   10

TABLE 1

BOP-Cl Coupling of N-Protected Amino Acids With Segments of the 2–7 Peptides

| Compound | Product Sequence | $[\alpha]_D(CHCl_3)$ | Yield(%) |
|---|---|---|---|
| 1 | BocMeLeu—AlaOBzl | −67.0° (1.0) | 74 |
| 2 | BocMeAla—AlaOBzl | −65.2° (1.5) | 66 |
| 3 | BocVal—MeLeuAlaOBzl | −97.2° (1.0) | 76 |
| 4 | BocVal—MeAlaAlaOBzl | −86.0° (1.7) | 90 |
| 5 | BocMeLeu—ValMeLeuAlaOBzl (SEQ ID NO:22) | −126.7° (1.0) | 95 |
| 6 | BocMeLeu—VMeAlaAlaOBzl (SEQ ID NO:23) | −136.0° (0.82) | 24 |
| 7 | BocMeAla—ValMeAlaAlaOBzl (SEQ ID NO:3) | −116.0° (0.9) | 22 |
| 8 | BocAbuSar—MeLeuValMeLeuAlaOBzl (SEQ ID NO:24) | −128.1° (1.0) | 56 |
| 9 | BocAbuSar—MeLeuValMeAlaAlaOBzl (SEQ ID NO:25) | −124.8° (0.5) | 92 |
| 10 | BocAbuSar—MeAlaValMeAlaAlaOBzl (SEQ ID NO:22) | −128.0° (0.7) | 98 |

The line (—) indicates site of new peptide bond formed from acid-amine coupling.

TABLE 2

Opticals rotation and yields of aminopeptide fragments

| Compound | Product Sequence | $[\alpha]_D(c,CHCl_3)$ | Yield(%) |
|---|---|---|---|
| 1 | H—MeLeuAlaOBzl | −44.5° (1.0) | 96 |
| 2 | H—MeAlaAlaOBzl | −24.8° (0.66) | 96 |
| 3 | H—ValMeLeuAlaOBzl | −102.0° (1.0) | 98 |
| 4 | H—ValMeAlaAlaOBzl | −45.4° (1.2) | 98 |
| 5 | H—MeLeuValMeLeuAlaOBzl (SEQ ID NO:22) | −130.9° (1.0) | 99 |
| 6 | H—MeLeuValMeAlaAlaOBzl (SEQ ID NO:23) | −101.0° (1.1) | 94 |
| 7 | H—MeAlaValMeAlaAlaOBzl (SEQ ID NO:2) | −112.0° (0.95) | 96 |
| 8 | H—AbuSarMeLeuValMeLeuAlaOBzl (SEQ ID NO:24) | −108.9° (1.27) | 92 |
| 9 | H—AbuSarMeLeuValMeAlaAlaOBzl (SEQ ID NO:25) | −126.7° (0.12) | 96 |
| 10 | H—AbuSarMeAlaValMeAlaAlaOBzl (SEQ ID NO:26) | −102.2° (0.9) | 98 |

TABLE 3

Physical properties of CsA analogs and their linear undecapeptide intermediates

| Compound | Structure[b] | $R_f$ (%)[a] | $[\alpha]_D(c,CHCl_3)$ | Yield(%) |
|---|---|---|---|---|
| 1 | [MeL(OH)$^1$] | 0.53(50) | −102.1° (0.73) | 62 |
| 2 | [MeL(OH)$^1$,MeA$^6$] | 0.49(50) | −122.0° (0.2) | 56 |
| 3 | [MeL(OH)$^1$,MeA$^{4,6}$] | 0.67(60) | −146.7° (0.02) | 34 |
| 4 | [MeL(OH)$^1$,D—Lys(Boc)$^8$] | 0.31(50) | −133.1° (1.9) | 62 |
| 5 | [MeL(OH)$^1$,D—MeVal$^{11}$] | 0.71(40) | −103.2° (2.5) | 32 |
| 6 | [MeL(OH)$^1$] | 0.49(50) | −200.0° (0.04) | 41 |
| 7 | [MeL(OH)$^1$,MeA$^6$] | 0.34(40) | −215.0° (0.2) | 56 |
| 8 | [MeL(OH)$^1$,MeA$^{4,6}$] | 0.53(60) | −247.5° (0.05) | 69 |
| 9 | [MeL(OH)$^1$,d-Lys(BOC)$^8$] | 0.47(50) | −182.5° (0.04) | 74 |
| 10 | [MeL(OH)$^1$,D—MeVal$^{11}$] | 0.54(50) | −162.5° (0.04) | 46 |

[a]TLC (% acetone/hexane).
[b]Abbreviated symbol: A = Ala; L = Leu.

TABLE 4

Chemical Shifts of Oxazolidinone Diastereomers

| Oxazolidinone | Chemical Shift δ (Coupling Constant J) | | | |
|---|---|---|---|---|
| | H-4 | H-5 | N—Me | O—Me |
| erythro- | 4.39(d, J=6.7) | 4.61(t, J=6.7) | 2.48 | 3.78 |
| threo- | 3.94(d, J=4.8) | 4.21(dd, J=4.8, 6.7) | 2.92 | 3.82 |

TABLE 5

Immunostimulatory Data

| Compound | Concentration (ug/ml) | Counts Per Minute + Std Dev |
|---|---|---|
| CsA | 10 | 1806 ± 834 |
| | 1 | 2815 ± 774 |
| | 0.1 | 3171 ± 332 |
| | 0.01 | 13339 ± 3283 |
| | 0.001 | 15248 ± 3898 |
| [L—MeLeu (3-OH)$^1$, MeAla$^{4,6}$]—CsA | 10 | 69959 ± 5978 |
| | 1 | 42779 ± 3396 |
| | 0.1 | 26646 ± 4236 |
| | 0.01 | 23615 ± 6484 |
| | 0.001 | 25773 ± 9147 |
| Media Control | | 40222 ± 7183 |
| Diluent Control | | 32279 ± 9205 |
| Unstimulated | | 1032 ± 453 |

TABLE 6

Immunostimulatory Data

| Subject | Concentration (ug/ml) | Counts Per Minute + Std Dev |
|---|---|---|
| Donor 1 | 20 | 75500 ± 3425 |
| | 10 | 69000 ± 1230 |
| | 5 | 53300 ± 8723 |
| | 2.5 | 60800 ± 3170 |
| | 1.25 | 58200 ± 1881 |
| | MediaControl | 51230 ± 4176 |
| | Diluent Control | 74000 ± 982 |
| Donor 2 | 20 | 62910 ± 9833 |
| | 10 | 36420 ± 6615 |
| | 5 | 30400 ± 7417 |
| | 2.5 | 25150 ± 902 |
| | 1.25 | 27300 ± 6925 |
| | MediaControl | 24550 ± 15196 |
| | Diluent Control | 33287 ± 2610 |
| Donor 3 | 20 | 61500 ± 7037 |
| | 10 | 47670 ± 10127 |
| | 5 | 56172 ± 4973 |
| | 2.5 | 50300 ± 9449 |
| | 1.25 | 50510 ± 3276 |
| | MediaControl | 49051 ± 13000 |
| | Diluent Control | 63042 ± 9720 |
| Donor 4 | 20 | 39062 ± 5324 |
| | 10 | 35200 ± 2543 |
| | 5 | 43060 ± 7950 |
| | 2.5 | 36507 ± 16397 |
| | 1.25 | 33800 ± 716 |
| | MediaControl | 23340 ± 7127 |
| | Diluent Control | 38200 ± 6969 |
| Donor 5 | 20 | 32000 ± 5324 |

TABLE 6-continued

Immunostimulatory Data

| Subject | Concentration (ug/ml) | Counts Per Minute + Std Dev |
|---|---|---|
|  | 10 | 16700 ± 881 |
|  | 5 | 24500 ± 4180 |
|  | 2.5 | 16400 ± 1720 |
|  | 1.25 | 13600 ± 994 |
|  | MediaControl | 13528 ± 3727 |
|  | Diluent Control | 10642 ± 1820 |
| Donor 6 | 20 | 47160 ± 11635 |
|  | 10 | 44900 ± 6950 |
|  | 5 | 41523 ± 10595 |
|  | 2.5 | 40784 ± 1059 |
|  | 1.25 | 35870 ± 9692 |
|  | MediaControl | 38000 ± 13433 |
|  | Diluent Control | 37000 ± 8921 |
| Donor 7 | 20 | 37100 ± 15202 |
|  | 10 | 34550 ± 329 |
|  | 5 | 24550 ± 3045 |
|  | 2.5 | 22130 ± 982 |
|  | 1.25 | 46162 ± 386 |
|  | MediaControl | 15500 ± 3830 |
|  | Diluent Control | 28050 ± 2706 |
| Donor 8 | 20 | 62713 ± 2247 |
|  | 10 | 45500 ± 10570 |
|  | 5 | 46670 ± 728 |
|  | 2.5 | 61846 ± 21866 |
|  | 1.25 | 46162 ± 386 |
|  | MediaControl | 40168 ± 7319 |
|  | Diluent Control | 46130 ± 10145 |

TABLE 7

Evaluation of Biological Activities of Novel CsA Analogs

| Mode | Result | Interpretation/Next Step |
|---|---|---|
| I | +inhib | Compound is immunosuppressive. |
| I | −inhib | Compound is not immunosuppressive/Evaluate in Modes II, III, and IV. |
| II | +inhib | Compound is a cyclophilin inhibitor and may also inhibit HIV replication/Evaluate directly for HIV inhibition as well as in Modes III and IV for additional utility. |
| II | −inhib | Compound is not a cyclophilin inhibitor and will not inhibit HIV replication/Evaluate in Modes III and IV for additional utility. |
| III | +inhib | Compound is an hsp70 inhibitor and may also inhibit other viral infections such as rabies and hepatitis B/Evaluate directly for viral inhibition as well as in Mode IV for additional utility. |
| III | −inhib | Compound is not an hsp inhibitor and will not inhibit rabies and hepatitis B infections/Evaluate in Mode IV for additional utility. |
| IV | +inhib | Compound is a protease inhibitor (HIVP inhibitor). |
| IV | −inhib | Compound is not a protease inhibitor (HIVP inhibitor). |

Key: +inhib = process inhibited; −inhib = process not inhibited.

We claim:

1. An immunostimulatory analog of cyclosporin having the structure shown in FIG. 3.

* * * * *

UNITED STATES PATENT AND TRADEMARK OFFICE
CERTIFICATE OF CORRECTION

PATENT NO. : 5,639,852
DATED : 06/17/97
INVENTOR(S) : Daniel H. Rich *et al.*

It is certified that error appears in the above-indentified patent and that said Letters Patent is hereby corrected as shown below:

In col. 1, line 2, in the line between "IMMUNOSTIMULATORY AGENTS" and FIELD OF THE INVENTION please insert --This invention was made with United States government support awarded by NIH grants RR-00167, AI-33237, and AR-32007. The United States Government has certain rights in this invention--.

In col. 2, line 34, after "Factor" please delete "a" and insert --α--.

In col. 4, line 7, please delete "(SEQ ID NOS:12-25)" and insert --(SEQ ID NOS:2,10,11)--.

In col. 4, line 11, please delete "[MeLeu(3-OH)$^1$]CsA" and insert --[MeLeu$^1$]CsA--.

In col. 7, line 23, please delete "(SEQ ID NOS:3) tetrapeptide" and insert --tetrapeptide (SEQ ID NO:3)--.

In col. 7, line 23, after "an" please delete "a" and insert --α--.

In col. 7, line 54, please delete "(SEQ ID NO:4)" and insert --(SEQ ID NO:5)--.

In col. 9, line 47, after "with" please delete "to".

In col. 10, line 7, please delete "a-aminobutyric acid" and insert --α-aminobutyric acid--.

Figure 4:
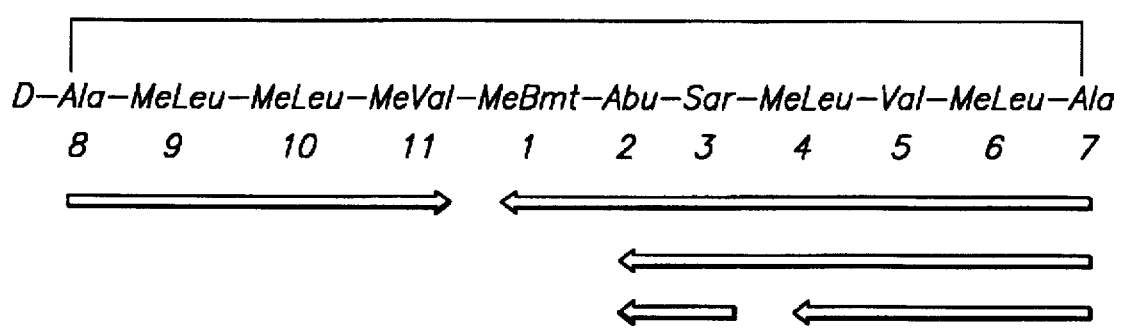
FIG. 4 is a schematic outlining the synthetic strategy used to synthesize Cyclosporin analogs (SEQ ID NO:1).

In col. 11, line 6, after "FIG. 4" please insert -- (SEQ ID NO:1)--.

In col. 11, line 57, after "(FIG. 11)" please insert --(SEQ ID NOS:5-7)--.

In col. 14, line 23 please delete "4°-6°" and insert --4-6°--.

In col. 15, line 63, please delete "A solution" and insert --To a solution--.

UNITED STATES PATENT AND TRADEMARK OFFICE
CERTIFICATE OF CORRECTION

PATENT NO. : 5,639,852
DATED : 06/17/97
INVENTOR(S) : Daniel H. Rich et al.

It is certified that error appears in the above-indentified patent and that said Letters Patent is hereby corrected as shown below:

In col. 17, line 14, please delete "2S,3R)" and insert --(2S,3R)--.

In col. 17, line 28, please delete "HLeu" and insert --H-Leu--.

In col. 18, line 43, please delete "12-26" and insert --12-20--.

In col. 49, Table 1, line 10, please delete "(SEQ ID NO:22)" and insert --(SEQ ID NO:26)--.

In col. 51, Table 2, line 7, please delete "(SEQ ID NO:2" and insert --(SEQ ID NO:2)--.

In col. 51, Table 2, line 9, please delete "(SEQ ID NO:25" and insert --(SEQ ID NO:25)--.

In col. 51, Table 2, line 10, please delete "(SEQ ID NO:26" and insert --(SEQ ID NO:26)--.

Signed and Sealed this

Thirtieth Day of September, 1997

BRUCE LEHMAN

Attest:

Attesting Officer

Commissioner of Patents and Trademarks